(12) United States Patent
Hayano et al.

(10) Patent No.: US 7,663,122 B2
(45) Date of Patent: Feb. 16, 2010

(54) LASER ANALYTICAL INSTRUMENT, LASER ANALYTICAL METHOD, AND GAS LEAK INSPECTION INSTRUMENT

(75) Inventors: Ryugo Hayano, 1-7-803, Hiroo 4-chome, Shibuya-ku, Tokyo (JP) 150-0012; Masaki Hori, 18-9, Minami-Ogikubo 2-chome, Suginami-ku, Tokyo (JP) 167-0052

(73) Assignees: Ryugo Hayano, Tokyo (JP); Masaki Hori, Tokyo (JP); Honda Motor Co., Ltd., Tokyo (JP)

( * ) Notice: Subject to any disclaimer, the term of this patent is extended or adjusted under 35 U.S.C. 154(b) by 160 days.

(21) Appl. No.: 11/632,377

(22) PCT Filed: Jul. 13, 2005

(86) PCT No.: PCT/JP2005/012942

§ 371 (c)(1),
(2), (4) Date: Jan. 12, 2007

(87) PCT Pub. No.: WO2006/006628

PCT Pub. Date: Jan. 19, 2006

(65) Prior Publication Data

US 2008/0121814 A1      May 29, 2008

(30) Foreign Application Priority Data

Jul. 14, 2004   (JP) .................... 2004-207794

(51) Int. Cl.
*G01J 1/58* (2006.01)
(52) U.S. Cl. .................................. 250/458.1
(58) Field of Classification Search ........... 250/288, 250/283, 459.1, 492.1, 458.1
See application file for complete search history.

(56) References Cited

U.S. PATENT DOCUMENTS 4,166,219 A * 8/1979 Ausschnitt et al. ....... 250/423 P (Continued)

FOREIGN PATENT DOCUMENTS

EP          1324021 A1 * 7/2003

(Continued)

OTHER PUBLICATIONS

Haugen, Harold K and Othonos, Andreas S., Fluorescence studies of multiple-photon ionization process: four- and five-photon ionization of Sr at wavelengths of 558-590nm, Physical Review A, Apr. 1, 1989, vol. 39., No. 7, p. 3392-3400.
International Preliminary Examination Report dated Oct. 3, 2006 in parent case PCT/JP2005/012942.

*Primary Examiner*—David P Porta
*Assistant Examiner*—Djura Malevic
(74) *Attorney, Agent, or Firm*—Lahive & Cockfield, LLP; Anthony A. Laurentano

(57) ABSTRACT

Laser light generated from laser light generating means (10) is fed through laser light transfer means (11) including a demagnification optical system (23) so as to be condensed in a part Ex where an object gas of analysis exists. The laser light is imparted with energy for causing a multiple photon excitation phenomenon or a multiple photon ionization phenomenon of gas in the condensed part Ex. The energy of the laser light is large enough for 17 eV or higher energy to be injected into a hydrogen molecule when the object gas of analysis is hydrogen and for 23 eV or higher energy to be injected into a helium atom when the object gas of analysis is helium. For example, the intensity of the laser light in the condensed part Ex is $10^{14}$ W/cm$^2$ or higher. This provides a laser analytical instrument capable of observing various types of gas through an inexpensive and simple arrangement.

15 Claims, 6 Drawing Sheets

U.S. PATENT DOCUMENTS

| | | | | |
|---|---|---|---|---|
| 4,655,890 | A * | 4/1987 | Robinson et al. | 204/157.22 |
| 5,110,204 | A * | 5/1992 | Miles et al. | 356/28 |
| 6,465,795 | B1 * | 10/2002 | Madonado et al. | 250/492.2 |
| 6,657,721 | B1 * | 12/2003 | Palleschi et al. | 356/318 |
| 2003/0218745 | A1 * | 11/2003 | Benicewicz et al. | 356/318 |
| 2004/0150887 | A1 * | 8/2004 | Hirai | 359/626 |
| 2008/0090110 | A1 * | 4/2008 | Kizaki | 429/13 |

FOREIGN PATENT DOCUMENTS

| | | |
|---|---|---|
| JP | 05-288813 | 11/1993 |
| JP | 08-075651 | 3/1996 |
| JP | 09-292341 | 11/1997 |
| JP | 09-304280 | 11/1997 |
| JP | 10-132740 | 5/1998 |
| JP | 2001-147225 | 5/2001 |
| JP | 2002-328196 | 11/2002 |
| JP | 2003-229148 | 8/2003 |
| JP | 2004-053294 | 2/2004 |
| JP | 2004-265667 | 9/2004 |
| WO | WO-99-49301 | 9/1999 |
| WO | WO-02/21109 | 3/2002 |

* cited by examiner

FIG. 6
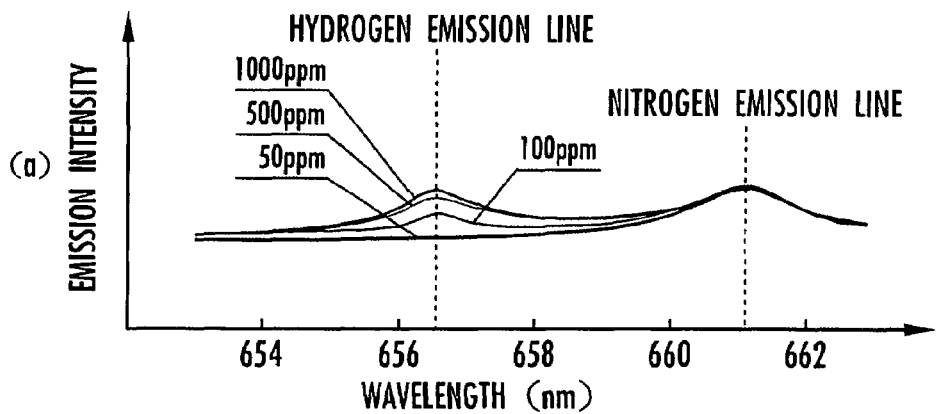
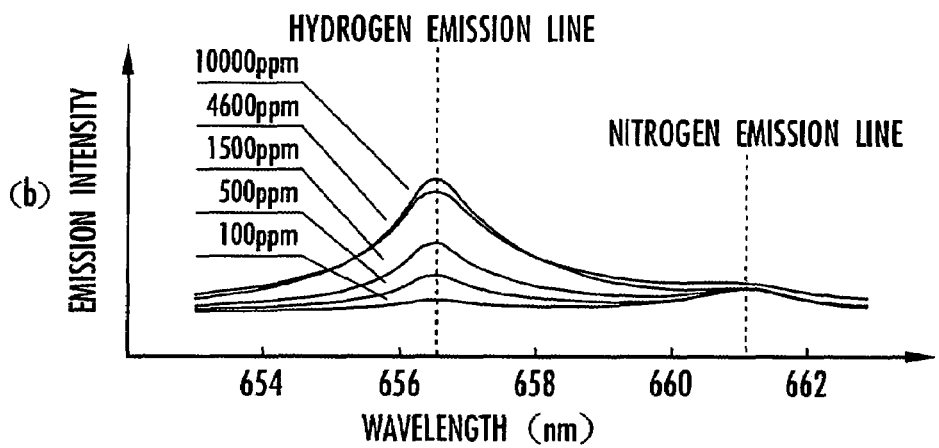
FIG. 7
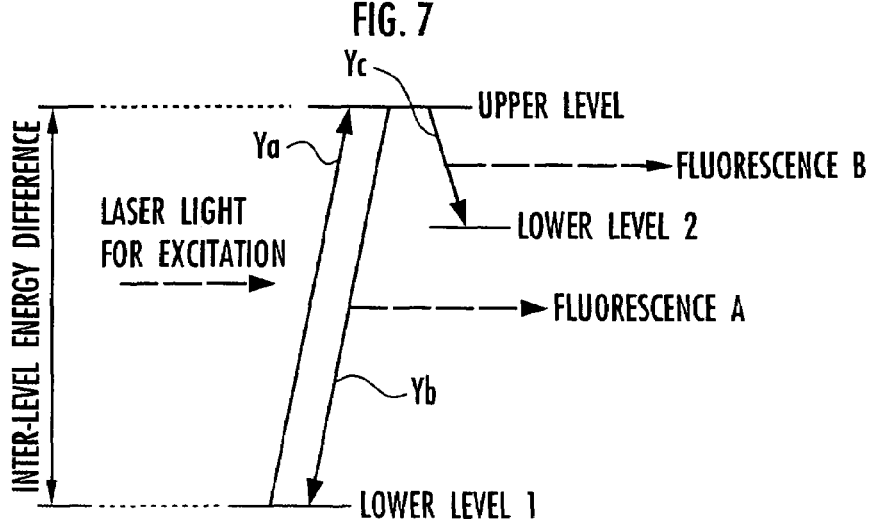

LASER ANALYTICAL INSTRUMENT, LASER ANALYTICAL METHOD, AND GAS LEAK INSPECTION INSTRUMENT

RELATED APPLICATIONS

This application is a 35 U.S.C. 371 national stage filing of International Application No. PCT/JP2005/012942, filed 13 Jul. 2005, which claims priority to Japanese Patent Application No. 2004-207794 filed on 14 Jul. 2004 in Japan. The contents of the aforementioned applications are hereby incorporated by reference.

TECHNICAL FIELD

The present invention relates to an instrument and method for analyzing gas using laser light and to an instrument for inspecting a fuel cell stack or a hydrogen supply/discharge system for supplying or discharging hydrogen to or from the fuel cell stack for a gas leak by using laser light.

BACKGROUND ART

There is already known a method of analyzing whether there is a specific type of object gas of analysis, gas concentration or the like by exciting the gas using laser light to produce fluorescence and analyzing the state (the wavelength, the intensity of the wavelength, and so forth) of the fluorescence (for example, refer to Japanese Patent Laid-Open No. Hei 8 (1996)-75651 (hereinafter, referred to as Patent Document 1)). The outline of the theory of operation of this method is now described with reference to FIG. 7. The object gas of analysis or plasma of the gas is irradiated with laser light for excitation in order to allow an atom in a lower level 1, which is a normal energy level (ground level), among atoms constituting the gas or plasma to absorb the energy of the laser light, by which the atom is excited to an upper level as indicated by an arrow Ya. In this instance, the wavelength of the laser light is set to the same level as the wavelength corresponding to the energy difference between the lower level 1 and the upper level (the wavelength is proportional to a reciprocal of the energy difference), that is the wavelength (resonance wavelength) corresponding to the energy to be absorbed when the atom is excited from the lower level 1 to the upper level. Therefore, the energy absorbed by the atom during the excitation is equal to energy of a photon of the laser light for excitation.

The gas or plasma excited to the upper level as described above is thereafter deexcited to the lower level 1 or 2 as indicated by an arrow Yb or Yc and produces fluorescence A or B during the deexcitation. In this instance, it is assumed that the lower level 2 exists between the lower level 1 and the upper level. In the analytical method as described in the Patent Document 1, the fluorescence A or B is picked up and the state (the intensity or the like) thereof is analyzed.

In addition, as an analytical method applicable only if the object gas of analysis has a molecular structure, the Raman scattering method (the spontaneous Raman scattering or stimulated Raman scattering (CARS)) is also conventionally known (for example, refer to Japanese Patent Laid-Open No. Hei 9 (1997)-292341 (hereinafter, referred to as Patent Document 2)). The Raman scattering method includes rotationally or vibrationally exciting molecules using laser light and analyzing the state of light scattered from the molecules (scattered light) during the excitation.

Furthermore, there is already known a method of detecting visualized hydrogen by visualizing hydrogen using a hydrogen visualization agent such as iodate ion solution to react iodine, which has been generated by reacting the hydrogen visualization agent with the hydrogen, with starch (for example, refer to Japanese Patent Laid-Open No. 2001-147225 (hereinafter, referred to as Patent Document 3)).

On the other hand, for example, regarding a fuel cell stack, it has been required to detect a gas leak before shipment or the like of the fuel cell stack since the gas leak from its body part or a pipe connected thereto leads to a reduction in generating efficiency or other troubles.

In the conventional fluorescence analysis method as disclosed in the Patent Document 1, the wavelength of the laser light emitted for irradiation needs to be the same as the wavelength corresponding to the inter-level energy difference of the atom or plasma as described above. Therefore, the wavelength of the laser light needs to be varied according to the type of gas to be detected (gas for producing fluorescence). Accordingly, the conventional fluorescence analysis method has a problem that it requires a device for varying the wavelength of the laser light when analyzing various types of gas using the conventional fluorescence analysis method, which leads to a complicated device configuration and to an increase in device cost. Furthermore, where gas is changed to plasma (dissociated electrolytically) to increase the intensity of the produced fluorescence, it is necessary to use two laser devices, which leads to a more expensive and complicated device.

Moreover, in the conventional fluorescence analysis method, some types of gas (for example, hydrogen and helium) cannot be detected as a matter of fact for the reason described below. More specifically, hydrogen or helium has a large inter-level energy difference (10 eV or higher) and therefore the absorption wavelength for its excitation exists in an extreme vacuum ultraviolet region of 120 nm or less. Under present circumstances, there is no laser device or optical component that can easily generate laser light having a wavelength in the extreme vacuum ultraviolet region. Furthermore, the light in the extreme vacuum ultraviolet region is immediately absorbed and attenuated in the air and therefore it is very difficult to irradiate a desired position with that kind of light.

In addition, since hydrogen and helium are useful as gas for use in leak inspection of a vacuum chamber or a fuel cell (fuel cell using hydrogen as fuel), it is required to develop a technology for optically detecting the hydrogen or helium without using the extreme vacuum ultraviolet light.

Moreover, the Raman scattering method as described in the Patent Document 2 is applicable only to some types of gas such as, for example, hydrogen molecules and nitrogen molecules, which are molecules that can be vibrationally or rotationally excited by irradiation with laser light and whose polarizability varies remarkably during the excitation. Accordingly, monoatomic gas (rare gas) such as helium or argon and a hydrogen atom cannot be detected by the Raman scattering method, by which the object gas of analysis is limited disadvantageously. Furthermore, in the spontaneous Raman scattering of the Raman scattering method, it is difficult to detect a very small amount of gas in the air. Still further, in the stimulated Raman scattering of the Raman scattering method, two different kinds of laser light are needed, which leads to a large-sized or complicated device configuration and to an expensive device disadvantageously.

Regarding the method using the hydrogen visualization agent as described in the Patent Document 3, it is difficult to supply the hydrogen visualization agent, which is liquid, only to a region within a specific small area of a fuel cell stack, for example, when it is attempted to detect a leakage of the hydrogen while supplying the hydrogen to the fuel cell stack. Therefore, it is difficult to identify the region of occurrence of a gas leak accurately using the method. Moreover, it has a problem of requiring a work for removing hydrogen visualization agent adhered to the surface of the fuel cell stack after the inspection.

In addition, it is also possible to soak the fuel cell stack in water and to supply the fuel cell stack with gas in this condition and to observe bubbles generated in the water in order to inspect the fuel cell stack for a gas leak. This method, however, requires a work for drying the fuel cell stack after the inspection.

In view of the above background, the present invention has been provided. Therefore, it is an object of the present invention to provide a laser analytical instrument and a laser analytical method capable of observing various types of gas through an inexpensive and simple arrangement independently of the type of gas employed. Furthermore, it is another object of the present invention to provide a gas leak inspection instrument capable of easily detecting a gas leak of a fuel cell stack or the like by using laser light.

DISCLOSURE OF THE INVENTION

The inventor of the present invention has found the following as a result of various experiments and considerations. Specifically, when laser light having an appropriate given wavelength is condensed so that the intensity of the laser light in the condensed part is relatively high, fluorescence can be generated in the condensed part by causing a multiple photon excitation phenomenon or a multiple photon ionization phenomenon, which is a nonlinear effect, independently of the type of gas existing there. The multiple photon excitation phenomenon or the multiple photon ionization phenomenon will be described here with reference to FIG. 1(a) and FIG. 1(b). FIG. 1(a) is a diagram showing a relation between the energy level transition and the occurrence of fluorescence of the multiple photon excitation phenomenon, and FIG. 1(b) is a diagram showing a relation between the energy level transition and the occurrence of fluorescence of the multiple photon ionization phenomenon.

Referring to FIG. 1(a), an object gas of analysis is irradiated with laser light for excitation having a given wavelength (for example, a wavelength in the visible light region) whose intensity is relatively high (for example, such intensity that the power density on a cross section perpendicular to an optical axis is $10^{14}$ W/cm$^2$ or higher). The atoms or molecules of the object gas of analysis are affected then by a very strong electric field that is generated by the action of the laser light, by which they each absorb a plurality of (for example, five to ten) photons at a time due to the nonlinear effect and are excited from a lower level 1 as a normal energy level to an upper level as indicated by multiple arrows Y1. This is the multiple photon excitation phenomenon. Each of the multiple arrows Y1 in FIG. 1(a) corresponds to the amount of energy of a single photon. The plurality of arrows Y1 are shown in this sense. The multiple photon excitation phenomenon occurs independently of the type of the object gas of analysis even if the wavelength of laser light is fixed. The atoms or molecules excited as described above are thereafter deexcited to the lower level 1 or 2 as indicated by an arrow Y2 or Y3, during which fluorescence A or B is produced. Since the energy level allowed for the atoms or molecules is determined by the type of the atoms or molecules, the wavelength of the fluorescence A or B depends on the type of the atoms or molecules. Accordingly, the state of the object gas of analysis can be analyzed by observing the fluorescence A or B.

Referring to FIG. 1(b), an object gas of analysis is irradiated with laser light for excitation having a given wavelength (for example, a wavelength in the visible light region) whose intensity is relatively high (for example, such intensity that the power density on the cross section perpendicular to the optical axis is $10^{14}$ W/cm$^2$ or higher). It is assumed here that the intensity of the laser light for excitation is higher than that of FIG. 1(a). The atoms or molecules whose energy level is at the lower level 1 absorb more photons so as to be excited to the continuous state (an energy state higher than the upper level described above) as indicated by an arrow Y1 and ionized (electrolytically dissociated to form a plasma). This is the multiple photon ionization phenomenon. Each of the multiple arrows Y1 in FIG. 1(b) corresponds to the amount of energy of a single photon. The multiple photon ionization phenomenon occurs independently of the type of the object gas of analysis even if the wavelength of laser light is fixed. For example, if the power density of the laser light is $10^{14}$ W/cm$^2$ or higher, the multiple photon ionization phenomenon can occur also in helium or other rare gas whose ionization energy is 25 eV or higher, in other words, chemically stable atoms. Incidentally, the multiple photon excitation phenomenon occurs, too, in the state where the multiple photon ionization phenomenon occurs.

Positive ions and electrons produced by the multiple photon ionization phenomenon as described above are thereafter recombined to form atoms or molecules again as indicated by the arrow Y4. Furthermore, their energy level is decreased to the lower level 1 or 2 by deexcitation as indicated by an arrow Y2 or Y3, during which fluorescence A or B is generated. Therefore, similarly to FIG. 1(a), the state of the object gas of analysis can be analyzed by observing the fluorescence A or B.

When focusing on, for example, hydrogen as the object gas of analysis, 15 eV or higher energy needs to be injected into one hydrogen molecule using the multiple photon in order to cause the multiple photon excitation phenomenon or the multiple photon ionization phenomenon in the single hydrogen molecule. More specifically, if 18 eV or higher energy is injected into one hydrogen molecule using a multiple photon, it is possible to cause the multiple photon ionization phenomenon of the hydrogen molecule. In the multiple photon ionization phenomenon of the hydrogen molecule, the hydrogen molecule is dissociated into a hydrogen ion and a hydrogen atom in the ground state, subsequently fluorescence is produced by recombination of the hydrogen ion (recombination with an electron) and deexcitation, and then the deexcited hydrogen atom is recombined with the hydrogen atom in the ground state to form a hydrogen molecule again. In addition, even in the case where energy less than 18 eV is injected into one hydrogen molecule using the multiple photon, it is possible to cause the multiple photon excitation phenomenon of the hydrogen molecule if energy is 15 eV or higher. In the multiple photon excitation phenomenon of the hydrogen molecule, the hydrogen molecule is dissociated into a hydrogen atom in the excited state having two or more principal quantum number and a hydrogen atom in the ground state. Thereafter, the hydrogen atom in the excited state is deexcited to produce fluorescence and the deexcited hydrogen atom is recombined with the hydrogen atom in the ground state to form a hydrogen molecule again.

Therefore, it is possible to cause the multiple photon excitation phenomenon or the multiple photon ionization phenomenon of the hydrogen molecule by injecting 15 eV or higher energy into each hydrogen molecule using the multiple photon. Note that, however, in the case where the energy is less than 17 eV even if 15 eV or higher energy is injected into the hydrogen molecule, the principal quantum number of the excited hydrogen atom remains 2. In this instance, the fluorescence produced by the deexcitation of the hydrogen atom is light having a wavelength in the extreme ultraviolet region, and therefore it is generally difficult to detect the fluorescence. On the other hand, in the multiple photon excitation phenomenon in which the injection energy into the hydrogen molecule is 17 eV or higher, the principal quantum number of the excited hydrogen atom is 3 or greater. In this instance, the fluorescence produced by the deexcitation of the hydrogen atom is light having a wavelength in the visible light region. Furthermore, the fluorescence produced by the multiple photon ionization phenomenon of the hydrogen molecule is light having a wavelength in the visible light region, too.

Therefore, if the object gas of analysis is hydrogen, the injection energy per hydrogen molecule using the multiple photon is preferably 17 eV or higher to produce the fluorescence having a wavelength in the visible light region.

When focusing on, for example, helium as the object gas of analysis, 21 eV or higher energy needs to be injected into one hydrogen molecule using the multiple photon in order to cause the multiple photon excitation phenomenon or the multiple photon ionization phenomenon in a single helium atom. More specifically, if 25 eV or higher energy is injected into one helium atom (helium is a monoatomic molecule) using the multiple photon, it is possible to cause the multiple photon ionization phenomenon of the helium atom. In the multiple photon ionization phenomenon of the helium atom, the helium atom is ionized and subsequently fluorescence is produced by recombination of the helium ion (recombination with an electron) and deexcitation, by which the helium atom in the ground state is formed again from the helium ion. In addition, even in the case where energy less than 25 eV is injected into one helium atom using the multiple photon, it is possible to cause the multiple photon excitation phenomenon of the helium atom if energy is 21 eV or higher. In the multiple photon excitation phenomenon of the helium atom, the helium atom is excited into a state of having a 2 or greater principal quantum number. Thereafter, the helium atom is deexcited to produce fluorescence and the helium atom in the ground state is formed again from the deexcited helium atom.

Therefore, it is possible to cause the multiple photon excitation phenomenon or the multiple photon ionization phenomenon of the helium atom by injecting 21 eV or higher energy into each helium atom using the multiple photon. Note that, however, in the case where the energy is less than 23 eV even if 21 eV or higher energy is injected into the helium atom, the principal quantum number of the excited helium atom remains 2. In this instance, the fluorescence produced by the deexcitation of the helium atom is light having a wavelength in the extreme ultraviolet region, and therefore it is generally difficult to detect the fluorescence. On the other hand, in the multiple photon excitation phenomenon in which the injection energy into the helium atom is 23 eV or higher, the principal quantum number of the excited helium atom is 3 or greater. In this instance, the fluorescence produced by the deexcitation of the helium atom is light having a wavelength in the visible light region. Furthermore, the fluorescence produced by the multiple photon ionization phenomenon of the helium atom is light having a wavelength in the visible light region, too.

Therefore, if the object gas of analysis is helium, the injection energy per helium atom using the multiple photon is preferably 23 eV or higher in order to produce the fluorescence having a wavelength in the visible light region.

Incidentally, if the power density of the laser light for excitation is $10^{14}$ W/cm$^2$ or higher, it is possible to cause the multiple photon excitation phenomenon or the multiple photon ionization phenomenon in all types of gas. Moreover, the laser light having the foregoing power density can be generated without any problem by using, for example, a known Nd:YAG laser (pulse laser) as a light source. Regarding, for example, hydrogen, even if the power density of the laser light for excitation is less than $10^{14}$ W/cm$^2$, it is possible to cause the multiple photon excitation phenomenon or the multiple photon ionization phenomenon. More specifically, if the laser light is assumed to have a wavelength in the ultraviolet region (for example, 213 nm), hydrogen can be excited or ionized by means of laser light for excitation whose power density is $10^{12}$ W/cm$^2$ or so. If the laser light is assumed to have a wavelength in the visible light region (for example, 532 nm), hydrogen can be excited or ionized by means of laser light for excitation whose power density is a little less than $10^{13}$ W/cm$^2$.

The present invention will be described below with consideration of the above.

To achieve the above object, there is provided in accordance with the present invention a laser analytical instrument for producing fluorescence having a wavelength corresponding to the type of object gas of analysis or to the type of each constituent gas of the object gas of analysis by exciting the object gas of analysis by laser light and then analyzing the state of the object gas of analysis on the basis of the state of the fluorescence, the laser analytical instrument comprising: a laser light generating means for generating laser light having a given wavelength; a demagnification optical system for emitting the laser light generated by the laser light generating means toward an area where the object gas of analysis exists so as to condense the laser light into a point in the area where the object gas of analysis exists; and a fluorescence analysis means for analyzing the state of the fluorescence, the received fluorescence being produced from the object gas of analysis in the condensed part of the laser light, wherein the laser light is imparted with energy for causing a multiple photon ionization phenomenon or a multiple photon excitation phenomenon of the object gas of analysis at least in the condensed part of the laser light (First invention).

To achieve the above object, there is provided in accordance with the present invention a laser analytical method for producing fluorescence having a wavelength corresponding to the type of object gas of analysis or to the type of each constituent gas of the object gas of analysis by exciting the object gas of analysis by laser light and then analyzing the state of the object gas of analysis on the basis of the state of the fluorescence, the laser analytical method comprising the steps of: emitting the laser light having a given wavelength toward an area where the object gas of analysis exists so as to condense the laser light into a point in the area where the object gas of analysis exists; causing a multiple photon ionization phenomenon or a multiple photon excitation phenomenon of the object gas of analysis by the energy of the laser light in the condensed part of the laser light and producing fluorescence from the object gas of analysis accompanying the phenomenon concerned; and receiving the produced fluorescence and analyzing the state of the fluorescence (12th invention).

According to the first and 12th inventions, the laser light is condensed in the area where the object gas of analysis exists and the laser light is imparted with the energy for causing the multiple photon ionization phenomenon or the multiple photon excitation phenomenon of the object gas of analysis at least in the condensed part. Therefore, even if the laser light has a given wavelength (fixed wavelength), it is possible to cause the multiple photon ionization phenomenon or the multiple photon excitation phenomenon in various types of gas existing in the condensed part and consequently to produce fluorescence having a wavelength corresponding to the type of the object gas of analysis in the condensed part or to the type of each constituent gas of the object gas of analysis. Therefore, it becomes possible to observe the state of the object gas of analysis (the concentration of the object gas of analysis, the concentration of each type of constituent gas of the object gas of analysis, the presence or absence of a specific type of gas, or the like) by receiving the fluorescence produced in the condensed part or analyzing the state of the fluorescence (the intensity (wavelength distribution) for each wavelength of the fluorescence, the intensity of the fluorescence having a specific wavelength, or the like)). In this instance, the laser light can be one having a given wavelength (a fixed wavelength) independently of the type of object gas of analysis or the type of each constituent gas of the object gas of analysis. Therefore, there is no need to use two lasers different in wavelength of laser light or to vary the wavelength of the laser light according to the type of the object gas of analysis. Therefore, an inexpensive and simple configuration can be achieved for the laser analytical instrument. In other words, according to the first or 12th invention, various types of gas can be analyzed with the inexpensive and simple configuration of the laser analytical instrument.

In the first and 12th inventions, it is preferable to employ a wavelength, for example, in the ultraviolet region or in the visible light region as the given wavelength of the laser light from a practical viewpoint.

In the first or 12th invention, if the object gas of analysis includes hydrogen, preferably the laser light is imparted with energy allowing injection of 17 electron-volts (17 eV) or higher energy into each of one or more hydrogen molecules existing in the condensed part (Second and 13th inventions).

According thereto, the fluorescence having a wavelength in the visible light region can be produced by the multiple photon excitation phenomenon or the multiple photon ionization phenomenon of the hydrogen molecule as described above. Therefore, the state of fluorescence can be analyzed without any problem and it is possible to easily observe the state of hydrogen (the presence or absence of hydrogen, the concentration of hydrogen, or the like), which has been difficult to perform by the conventional technique.

Furthermore, in the first or 12th invention, if the object gas of analysis includes helium, preferably the laser light is imparted with energy allowing injection of 23 electron-volts (23 eV) or higher energy into each of one or more helium atoms existing in the condensed part (Third and 14th inventions).

According thereto, the fluorescence having a wavelength in the visible light region can be produced by the multiple photon excitation phenomenon or the multiple photon ionization phenomenon of the helium atom as described above. Therefore, the state of fluorescence can be analyzed without any problem and it is possible to easily observe the state of helium (the presence or absence of helium, the concentration of helium, or the like), which has been difficult to perform by the conventional technique.

Furthermore, in the first or 12th invention, preferably a peak intensity in the condensed part of the laser light (more particularly, a peak intensity on the cross section perpendicular to the optical axis of the laser light) is $10^{14}$ W/cm$^2$ or higher (Fourth or 15th invention).

According to the fourth and 15th inventions, it is possible to cause the multiple photon excitation phenomenon or the multiple photon ionization phenomenon in all types of gas independently of the type of the object gas of analysis or the type of each constituent gas of the object gas of analysis. In this instance, preferably the wavelength of the laser light is, for example, a visible light wavelength.

Incidentally, according to the fourth and 15th inventions, 17 eV or higher energy can be injected into each of the hydrogen molecules and 23 eV or higher energy can be injected into each of the helium atoms by the multiple photon of the laser light in the condensed part. Therefore, even if one of hydrogen and helium is included in the object gas of analysis, it is possible to produce the fluorescence in the visible light region corresponding to the hydrogen or helium.

Particularly, in the first to fourth inventions, preferably a light source of the laser light generating means is formed by a pulse laser having a top-hat power density distribution on a cross section perpendicular to the optical axis of the laser light output from the light source (Fifth invention).

According to the fifth invention, it is possible to obtain a large intensity with a relatively simple light source arrangement as the peak intensity of the laser light emitted from the light source and consequently to obtain the intensity (preferably, $10^{14}$ W/cm$^2$ or higher) capable of causing the multiple photon excitation phenomenon or the multiple photon ionization phenomenon in various types of gas as the intensity (energy) of the laser light in the condensed part. As a power density distribution that can increase the peak intensity of the laser light, there is, for example, a Gaussian type as well as the top-hat type. The top-hat type, however, is more preferable to increase the peak intensity as much as possible.

In the fifth invention, it is especially preferable to provide a phase conjugation laser transfer optical system in an optical path of the laser light from the laser light generating means to the demagnification optical system (Sixth invention).

In other words, the phase conjugation laser transfer optical system transfers the laser light efficiently in such a way as to maintain a power density distribution of the input laser light (the power density distribution on the cross section perpendicular to the optical axis) by optically performing inverse transformation on light components of light components of the laser light input to the phase conjugation laser transfer optical system. Therefore, the laser light can be input to the demagnification optical system while maintaining the power density distribution (the top-hat type) of the laser light output from the light source by providing the above phase conjugation laser transfer optical system in the optical path.

More specifically, light components having various phases constituting a light beam interfere with each other generally in the process where laser light propagates through the air. Therefore, if the propagated distance is long, the power density distribution deteriorates. Consequently, even if the laser light immediately after being output from a laser resonator (light source) has an ideal power density distribution such as the top-hat or Gaussian type, energy in the center section of the laser light disperses toward the outside thereof after the laser light propagates a distance of several to tens of meters, for example, and the power density distribution of the laser light changes to a divergent form. In some cases, the power density distribution changes drastically to an undesirable form such as a prolate ellipsoid, toroidal, or rectangular form or a striped pattern during the laser light propagation. Since it is generally difficult to efficiently condense the laser light having the deteriorated power density distribution into a small point as described above, it becomes hard to produce fluorescence by irradiating gas with the laser light having the large intensity at a point distant from the laser resonator (light source) in this situation. Moreover, it is desired to enable measurement of the state (such as a concentration distribution) of the object gas of analysis such as hydrogen or helium that exists at the point distant from the light source, considering various uses of the present invention. The phase conjugation laser transfer optical system can accurately transfer and reproduce the power density distribution of the laser light output from the laser resonator (light source) at an arbitrary point distant from the laser resonator by arranging lenses, mirrors, and a vacuum tube in appropriate combination with each other. Therefore, it can solve the above problem that the density distribution of the laser light deteriorates. Consequently, the peak intensity of the laser light can be prevented from decreasing in the optical path of the laser light from the light source to the condensed part as far as possible. Therefore, while the peak intensity of the laser light output from the light source is limited to the minimum, the intensity (energy) of the laser light in the condensed part can be one capable of causing the multiple photon excitation phenomenon or the multiple photon ionization phenomenon in various types of gas (preferably, $10^{14}$ W/cm$^2$ or higher intensity). In other words, with a light source of the laser light having a relatively inexpensive and simple arrangement, the intensity (energy) of the laser light in the condensed part can be one capable of causing the multiple photon excitation phenomenon or the multiple photon ionization phenomenon in various types of gas (preferably, $10^{14}$ W/cm$^2$ or higher intensity).

According to a first alternative of the gas leak inspection instrument of the present invention, there is provided a gas leak inspection instrument for inspecting an inspection object having a gas passage inside for a gas leak by using one of the laser analytical instruments of the first to sixth inventions, the gas leak inspection instrument comprising means for supplying a given type of gas to the inspection object, wherein the laser light is emitted from the demagnification optical system in such a way that the condensed part of the laser light exists in the vicinity of the inspection objection in the supply state of the given type of gas (Seventh invention).

According to the seventh invention, it is possible to grasp the state of the fluorescence having a wavelength corresponding to the given type of gas (the intensity of the fluorescence having the wavelength) by analyzing the state of the fluorescence produced in the condensed part. Therefore, the leak state of the given type of gas (whether there is a gas leak or the leak rate thereof, or the like) can be observed. Since the laser analytical instrument according to one of the first to sixth inventions is used in this instance, the inspection object can be easily inspected for a gas leak with an inexpensive and simple arrangement. In addition, gas can be selected out of various types of gas regarding the type of gas supplied to the inspection object, which increases the degree of freedom in design of the gas leak inspection instrument.

In the seventh invention, preferably the inspection object is a fuel cell stack, a hydrogen supply system for supplying hydrogen to the fuel cell stack, or a hydrogen discharge system for discharging the hydrogen from the fuel cell stack and the gas supplied to the inspection object is hydrogen or helium (Eighth invention).

According to the eighth invention, it is possible to inspect the fuel cell stack, the hydrogen supply system for supplying hydrogen to the fuel cell stack, or the hydrogen discharge system for discharging hydrogen from the fuel cell stack for a gas leak without adversely affecting a polyelectrolyte membrane inside the fuel cell stack. Furthermore, since almost no hydrogen or helium is contained as gas in the normal air at all, the gas leak inspection can be performed also in the air (even if the inspection object is left open to the air). Incidentally, as examples of hydrogen supply system or the hydrogen discharge system, there are a hydrogen storage container, a hydrogen supply pump, and a pipe.

In the seventh or eighth invention, particularly where the gas supplied to the inspection object is hydrogen, preferably the laser light is emitted toward the vicinity of the inspection object at least in the state where the inspection object is housed in a closed chamber filled with nitrogen (Ninth invention).

More specifically, if hydrogen is used as gas to be supplied to the inspection object and the gas leak inspection is performed in the air, it is sometimes difficult to detect a minute amount of hydrogen leakage due to the effect of hydrogen produced by dissociation of water vapor caused by the laser light particularly at a high humidity of the atmospheric air. According to the ninth invention, however, the gas leak inspection is performed in the closed chamber filled with nitrogen, and therefore even if the amount of hydrogen leakage is relatively minute, the minute amount of hydrogen can be detected. In other words, it is possible to increase the resolution of the concentration of the detectable hydrogen.

Furthermore, in the seventh to ninth inventions, preferably the gas leak inspection instrument further comprises moving means for relatively moving the condensed part of the laser light with respect to the inspection object (Tenth invention).

According thereto, the gas leak inspection can be performed in a numerous regions of the inspection object with the condensed part of the laser light scanned relative to the inspection object. To identify the region of occurrence of a gas leak, preferably the inspection object is fixed (to be immovable) and the demagnification optical system or the like is moved so that the condensed part of the laser light is moved relative to the inspection object.

In the tenth invention, the fluorescence analysis means includes means for generating image data indicating a relation between a relative position of the condensed part of the laser light with respect to the inspection object and the intensity of fluorescence having a wavelength corresponding to the given type of gas in the fluorescence produced in the condensed part (11th invention).

According thereto, a spatial distribution state of the gas leakage can be grasped based on the image data, and therefore it is possible to easily identify the region of the gas leakage of the inspection object.

According to a second alternative of the gas leak inspection instrument of the present invention, there is provided a gas leak inspection instrument for inspecting an inspection object for a gas leak, the inspection object being a fuel cell stack, a hydrogen supply system for supplying hydrogen to the fuel cell stack, or a hydrogen discharge system for discharging the hydrogen from the fuel cell stack, the gas leak inspection instrument comprising: a laser light irradiation means for emitting at least one beam of laser light toward the vicinity of the inspection object; a means for supplying a given type of gas to the inspection object; and an analysis means for analyzing the state of a received light, the received light being generated in the vicinity of the inspection object in the state where the given type of gas is supplied to the inspection object and laser light is emitted from the laser light irradiation means (16th invention).

According to the 16th invention, it is possible to observe the leak state of the given type of gas (whether there is a gas leak, the leak rate thereof, or the like) by analyzing the state (wavelength or intensity) of the light received by the analysis means. Since the inspection object (the fuel cell stack or the hydrogen supply/discharge system for supplying hydrogen to the fuel cell stack or discharging the hydrogen from the fuel cell stack) can be inspected for a gas leak without liquid adhering to the inspection object by using the laser light, there is no need to remove or dry the liquid adhering to the inspection object after the inspection. Therefore, the gas leak inspection can be easily performed for the inspection object.

In the 16th invention, the area in the vicinity of the inspection object can be irradiated with two beams of laser light as in the stimulated Raman scattering method. Alternatively, laser light having a wavelength corresponding to the given type of gas can be used as in the conventional fluorometry in which an atom is excited by a single photon. The hydrogen supply system or the hydrogen discharge system can be a hydrogen storage container, a hydrogen supply pump, a pipe, or the like.

In the 16th invention, preferably the gas leak inspection instrument further comprises moving means for relatively moving the irradiated position of the laser light with respect to the inspection object (17th invention).

According thereto, the gas leak inspection can be performed in a numerous regions of the inspection object with the laser light irradiated position scanned relative to the inspection object. To identify the region of occurrence of a gas leak, preferably the inspection object is fixed (to be immovable) and the laser light irradiated position is moved relative to the inspection object.

Furthermore, in the 17th invention, the fluorescence analysis means includes means for generating image data indicating a relation between a relative position of the laser light irradiated position with respect to the inspection object and the intensity of fluorescence having a wavelength corresponding to the given type of gas in the fluorescence produced in the condensed part (18th invention).

According thereto, a spatial distribution state of the gas leakage can be grasped based on the image data, and therefore it is possible to easily identify the region of the gas leakage of the inspection object.

BRIEF DESCRIPTION OF THE DRAWINGS

FIG. 6(a) and FIG. 6(b) are graphs showing measured data of the wavelength distributions of fluorescence produced when detecting hydrogen in nitrogen and hydrogen in air, respectively; and FIG. 7 is a diagram for explaining conventional fluorometry.

BEST MODE FOR CARRYING OUT THE INVENTION

A first embodiment of the present invention will be described below with reference to FIG. 2 and FIG. 3. This embodiment is an embodiment of a laser analytical instrument of the present invention and also an embodiment of a gas leak inspection instrument thereof.

Figure 1:
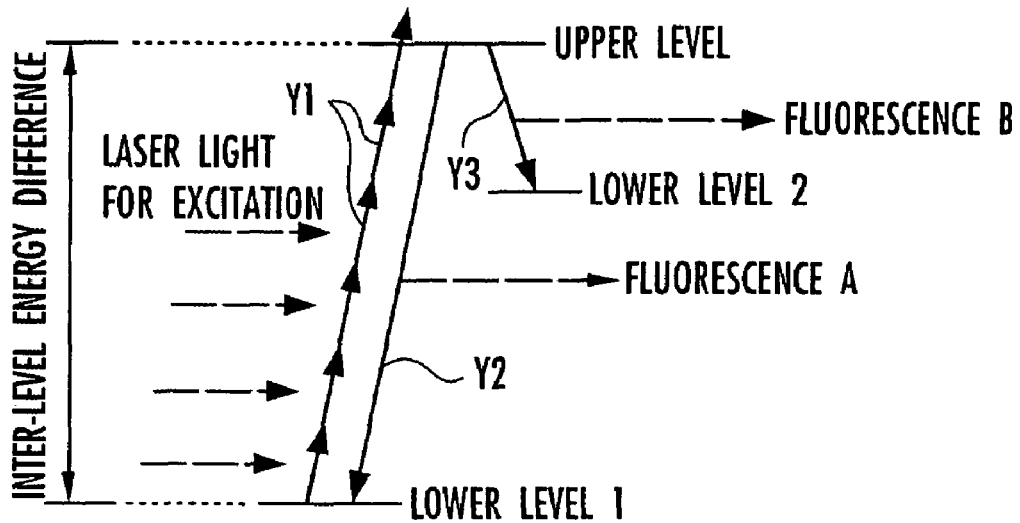
FIG. 1(a) and FIG. 1(b) are a diagram for explaining a multiple photon excitation phenomenon and a diagram for explaining a multiple photon ionization phenomenon, respectively, in the present invention.
Figure 1:
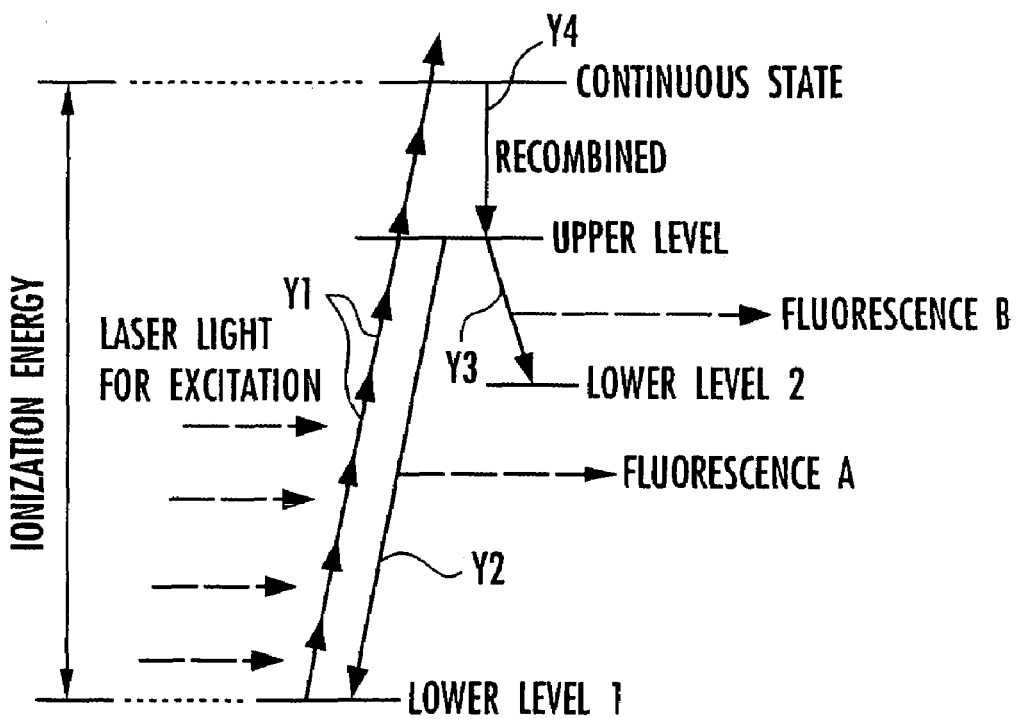
Figure 2:
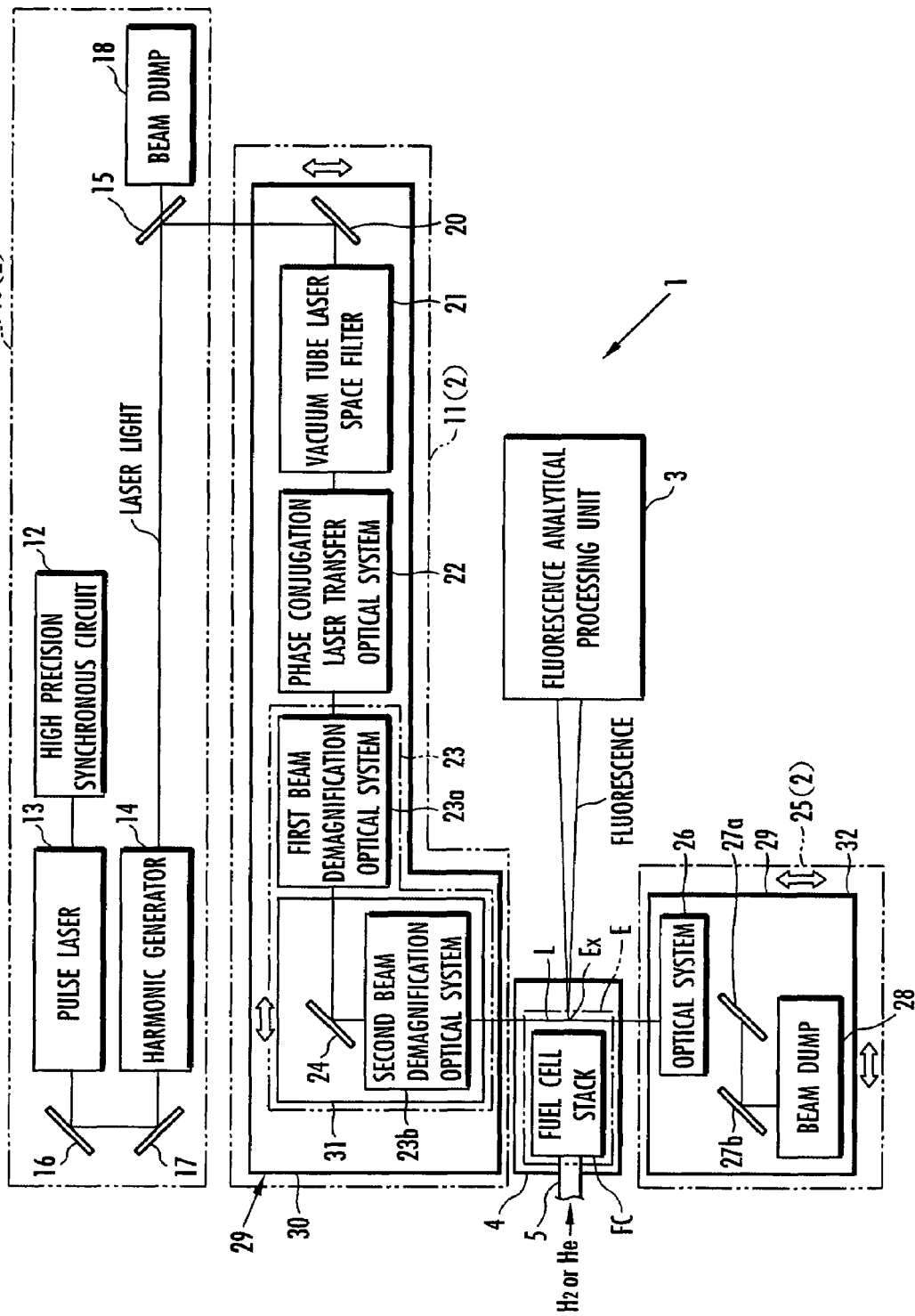
FIG. 2 is a block diagram showing the overall configuration of an instrument according to a first embodiment of a laser analytical instrument and a gas leak inspection instrument of the present invention.

Referring to FIG. 2, there is shown a block diagram illustrating the overall configuration of the instrument of this embodiment. This instrument 1 mainly includes a laser light generating/transfer unit 2 for generating laser light and guiding it to a given target inspection region E and a fluorescence analytical processing unit 3 for receiving fluorescence produced by gas using the laser light guided to the target inspection region E.

A base 4 is provided in a fixed manner in the target inspection region E, so that a fuel cell stack FC is placed as an inspection object in a fixed manner. A fuel cell stack FC generates electricity by being supplied with hydrogen as anode gas and air as cathode gas (more accurately, oxygen in the air) with a chemical reaction between them. The instrument 1 of this embodiment is configured to inspect a gas passage of the above-described fuel cell stack FC (a gas passage inside the fuel cell stack FC or a pipe channel in communication with the gas passage and connected to the outside of the fuel cell stack FC) for a gas leak. Moreover, the fuel cell stack FC placed on the base 4 is connected to a pipe 5 for supplying gas for the gas leak inspection to the fuel cell stack FC. In this embodiment, hydrogen or helium is used as gas for the gas leak inspection.

The laser light generating/transfer unit 2 includes laser light generating means 10 for generating and outputting laser light having a given wavelength and laser light transfer means 11 for guiding the light to the target inspection region E so as to condense the light in a given part Ex within the target inspection region E.

The laser light generating means 10 includes a high precision synchronous circuit 12, a pulse laser 13, a harmonic generator 14, and a harmonic split mirror 15. The high precision synchronous circuit 12 generates two types of electrical pulse signals and inputs them to the pulse laser 13 to oscillate the pulse laser 13.

The pulse laser 13 oscillates according to the electrical pulse signal input from the high precision synchronous circuit 12 to output pulsing laser light. The pulse laser 13 corresponds to a light source of the laser light. In this instance, the temporal fluctuation in oscillation of the pulse laser 13 relative to the electrical pulse signal is equal to or less than several nanoseconds. The pulse laser 13 is of the type of having a top-hat power density distribution on a cross section perpendicular to an optical axis of the output laser light and a Nd:YAG laser is used for the pulse laser 13 in this embodiment. The laser light output from the pulse laser 13 has a time width of a pulse of several nanoseconds or less, an intensity of 0.5 to 1 joule per pulse, a beam divergence of approx. 1.2 to 1.5 relative to the diffraction limit, and a wavelength of 1064 nm. Although the power density distribution of the laser light output from the pulse laser 13 is of the top-hat type in this embodiment, it can be of, for example, the Gaussian type. It is, however, preferable that the power density of the laser light is of the top-hat type to improve the peak intensity of the laser light as far as possible.

The laser light output from the pulse laser 13 is input to the harmonic generator 14 after its traveling direction (the optical axis direction) is reversed through two reflecting mirrors 16 and 17. The harmonic generator 14 is for use in converting the wavelength of the input laser light. More specifically, the harmonic generator 14, which is formed of a nonlinear optical crystal, converts a part of the input laser light to laser light having a wavelength of 1/n (n: 2 or a greater integer) of the wavelength of the input laser light (laser light having a harmonic frequency of the frequency of the input laser light) and then outputs it together with the laser light having the original wavelength. The wavelength of the laser light whose wavelength has been converted is one-half of the wavelength of the laser light output from the pulse laser 13, more specifically, 532 nm in this embodiment, which is a wavelength in the green region (a wavelength of visible light). The nonlinear optical crystal constituting the harmonic generator 14 is, for example, a BBO crystal (beta barium borate crystal) cut at a crystal angle of, for example, 22.8 degrees, having a length of the order of 5 to 10 mm.

The laser light output from the harmonic generator 14 is input to the harmonic split mirror 15. The harmonic split mirror 15 reflects the laser light whose wavelength has been converted in the harmonic generator 14 (the laser light having the wavelength of 532 nm), while transmitting laser light of other wavelengths. The laser light reflected by the harmonic split mirror 15 is finally output by the laser light generating means 10 in this embodiment.

The optical axis (traveling direction) of the laser light reflected by the harmonic split mirror 15 is oriented to a direction perpendicular to the optical axis of the laser light input to the harmonic split mirror 15. In addition, the laser light transmitted by the harmonic split mirror 15 is input to a beam dump 18. The beam dump 18 absorbs and attenuates energy of the input laser light.

More specifically, although the laser light generating means 10 outputs the laser light (532-nm wavelength) of a second higher harmonic wave of the laser light output from the pulse laser 13 in this embodiment, it can also output laser light having a wavelength of a third, fourth, or fifth higher harmonic wave of the laser light output from the pulse laser 13. As the pulse laser 13, it is also possible to use an excimer gas laser, a Nd:YLF laser, a titanium-sapphire laser, an attosecond laser, a femtosecond laser, and a picosecond laser, besides the Nd:YAG laser. In view of the maintenance and the reduction in size and weight of the laser, however, it is preferable to use a solid laser such as the Nd:YAG laser or the Nd:YLF laser. Furthermore, in view of the efficiency of gas excitation or ionization (electrolytic dissociation) or less penetration of stray light into the fluorescence analytical processing unit 3, it is also possible to generate and output ultraviolet laser light. In this instance, the harmonic generator 14 is used to generate the fifth higher harmonic wave laser light (wavelength of 213 nm) and the harmonic split mirror 15 is used to reflect the laser light having the wavelength.

The laser light (the laser light reflected by the harmonic split mirror 15) output from the laser light generating means 10 is supplied to the laser light transfer means 11.

The laser light transfer means 11 includes a reflecting mirror 20, a vacuum tube laser space filter 21, a phase conjugation laser transfer optical system 22, and a beam demagnification optical system 23. The laser light supplied from the laser light generating means 10 is changed in traveling direction thereof at 90 degrees by the reflecting mirror 20 and then input to the vacuum tube laser space filter 21. The vacuum tube laser space filter 21 shapes the transverse mode profile of the input laser light. The laser light after the shaping is transferred to the beam demagnification optical system 23 via the phase conjugation laser transfer optical system 22. As described above, the phase conjugation laser transfer optical system 22 maintains the power density distribution of the laser light input thereto as the top-hat or Gaussian type, which is the power density distribution of the laser light output from the laser light generating means 10, to prevent the peak intensity of the laser light from decreasing.

The beam demagnification optical system 23 is for use in narrowing (demagnifying) the beam diameter of the input laser light in the traveling direction. In this embodiment, the beam demagnification optical system 23 includes a first beam demagnification optical system 23a, a second beam demagnification optical system 23b, and a reflecting mirror 24 placed therebetween. The beam demagnification optical system 23 demagnifies the beam diameter of the laser light, which is supplied from the phase conjugation laser transfer optical system 22, by using the first beam demagnification optical system 23a and then changes the direction of the laser light to the direction toward the target inspection region E (the direction of crossing the target inspection region E) through the reflecting mirror 24. Thereafter, it further demagnifies the beam diameter by the second beam demagnification optical system 23b.

In this instance, the first beam demagnification optical system 23a and the second beam demagnification optical system 23b are configured so that the laser light output from the second beam demagnification optical system 23b (hereinafter, a reference character L is appended to the laser light) is condensed (focused) into a point (a region having a diameter of 50 to 100 μm or so) in a part Ex within the target inspection region E, which is apart from the second beam demagnification optical system 23b by a given distance on the optical axis of the laser light. The distance from the second beam demagnification optical system 23b to the part Ex where the laser light L is condensed (hereinafter, the part Ex is referred to as the condensed part Ex) can be set, for example, in a range of 0.3 to 10 m. In this embodiment, the laser light generating means 10 is constructed using the pulse laser 13 and the phase conjugation laser transfer optical system 22 is provided, by which an intensity of $10^{14}$ W/cm$^2$ or higher such as, for example, an intensity of $10^{15}$ to $10^{16}$ W/cm$^2$ is secured as a peak condensation intensity (a peak value of the intensity) of the laser light L in the condensed part Ex.

In this embodiment, the large intensity set in the condensed part Ex of the laser light L enables an occurrence of a multiple photon excitation phenomenon or a multiple photon ionization phenomenon, which is a nonlinear phenomenon that causes absorption of a numerous photons, in various types of gas (hydrogen, helium, nitrogen, oxygen, water vapor or the like) that exist in the condensed part Ex. Incidentally, the gas electrolytically dissociated and ionized by the multiple photon ionization phenomenon in the condensed part Ex has a life of several nanoseconds to several milliseconds. Thereafter, it is recombined and deexcited to return to the state of nonionic atoms or molecules. During this time, fluorescence having a wavelength (not always one wavelength for a single type of gas) corresponding to the type of gas occurs. Similarly, the gas excited by the multiple photon excitation phenomenon in the condensed part Ex is deexcited and during this time fluorescence having a wavelength corresponding to the type of gas occurs. The fluorescence scatters all around without directivity. Furthermore, in this embodiment, the large intensity provided in the condensed part Ex of the laser light L enables 17 eV or higher energy to be injected into each hydrogen molecule if hydrogen exists in the condensed part Ex and enables 23 eV or higher energy to be injected into each helium atom if helium exists in the condensed part Ex. In other words, the intensity of the laser light L in the condensed part Ex is so large for both of hydrogen and helium as to excite or ionize the hydrogen or helium into a state of causing visible fluorescence.

The laser light generating/transfer unit 2 further includes an optical system 26, a pair of reflecting mirrors 27a and 27b, and a beam dump 28 as laser light capturing means 25 for capturing the laser light L that has passed through the condensed part Ex. The laser light L having passed through the condensed part Ex is guided to the optical system 26 so as to be changed to parallel rays and then guided to the beam dump 28 via the reflecting mirrors 27a and 27b. The beam dump 28 then absorbs the energy of the laser light L to be attenuated. In addition, the beam dump 28 measures the intensity of the laser light L based on heat generation thereof (heat generated during the absorption of the energy of the laser light L).

The laser light transfer means 11 further includes an XY table 29 as moving means for moving the condensed part Ex of the laser light L within the target inspection region E along the surface of the fuel cell stack FC (or a pipe attached thereto) on the base 4 in the target inspection region E.

The XY table 29 includes a first moving table 30 movable by an electric motor, which is not shown, in an optical axis direction of the laser light output from the laser light generating means 10 and a second moving table 31 movable by an electric motor, which is not shown, in an optical axis direction (the direction perpendicular to the moving direction of the first moving table 30) of the laser light reflected by the reflecting mirror 20, with the first moving table 30 carrying the second moving table 31, the reflecting mirror 20, the vacuum tube laser space filter 21, the phase conjugation laser transfer optical system 22, and the first beam demagnification optical system 23a thereon so that they can move with the first moving table 30. Furthermore, the second moving table 31 also carries the reflecting mirror 24 and the second beam demagnification optical system 23b so that they can move with the second moving table 31. Therefore, the second beam demagnification optical system 23b moves horizontally by moving the first moving table 30 and the second moving table 31, which enables the condensed part Ex of the laser L output from the second beam demagnification optical system 23b to move along the surface of the fuel cell stack FC within the target inspection region E (the condensed part Ex relatively moves with respect to the fuel cell stack FC). In other words, the condensed part Ex of the laser L can be scanned within the target inspection region E by moving the first moving table 30 and the second moving table 31.

Although the XY table 29 has been used to move the condensed part of the laser light L in this embodiment, naturally it is possible to mount the laser light transfer means 11 on 3-axis moving means (for example, an XYZ table) so that the condensed part Ex of the laser light L can be moved spatially (three-dimentionally). In addition, it is also possible to move the condensed part Ex of the laser light L by moving only the beam demagnification optical system 23 of the laser light transfer means 11 or to move the condensed part Ex of the laser light L by swinging the second beam demagnification optical system 23b. Alternatively, the condensed part Ex in the optical axis direction of the laser light L can be moved by varying a focal position of the beam demagnification optical system 23 (or the second beam demagnification optical system 23b).

Moreover, the fuel cell stack FC can be moved by using the XY table without moving the laser light transfer means 11 and the beam demagnification optical system 23. If the fuel cell stack FC is moved, however, it easily leads to a deviation between the position of a gas leak and the moved position of the fuel cell stack FC when the gas leak occurs in the fuel cell stack FC. Therefore, the fuel cell stack FC is fixed to be immovable and the beam demagnification optical system 23 and others are movably arranged in this embodiment.

The laser light capturing means 25 is provided with a moving table 32 movable by an electric motor, which is not shown, in conjunction with the XY table 29 of the laser light transfer means 11, with the moving table 32 carrying the optical system 26, the pair of reflecting mirrors 27a and 27b, and the beam dump 28 thereon so that they can move with the moving table 32. The moving table 32 moves in the same direction as the XY table 29 of the laser light transfer means 11 in conjunction therewith, by which the optical system 26 is opposed to the second beam demagnification optical system 23b of the laser light transfer means 11 at all times.

The moving table 32 is only required to be movable so that the optical system 26 is opposed to the second beam demagnification optical system 23b of the laser light transfer means 11 at all times (so that the optical system 26 is located on the optical axis of the laser light L), and the moving table 32 need not always be movable in the 2-axis or 3-axis direction. For example, it can be movable only in the direction perpendicular to the optical axis of the laser light L.

The fluorescence analytical processing unit 3 receives fluorescence produced by the gas in the condensed part Ex of the laser light L and analyzes its wavelength distribution (spectrum distribution) or the like. The fluorescence analytical processing unit 3 corresponds to fluorescence analysis means in the first invention or to analysis means in the 16th invention. Referring to FIG. 3, there is shown a block diagram of the configuration of the fluorescence analytical processing unit 3.

Figure 3:
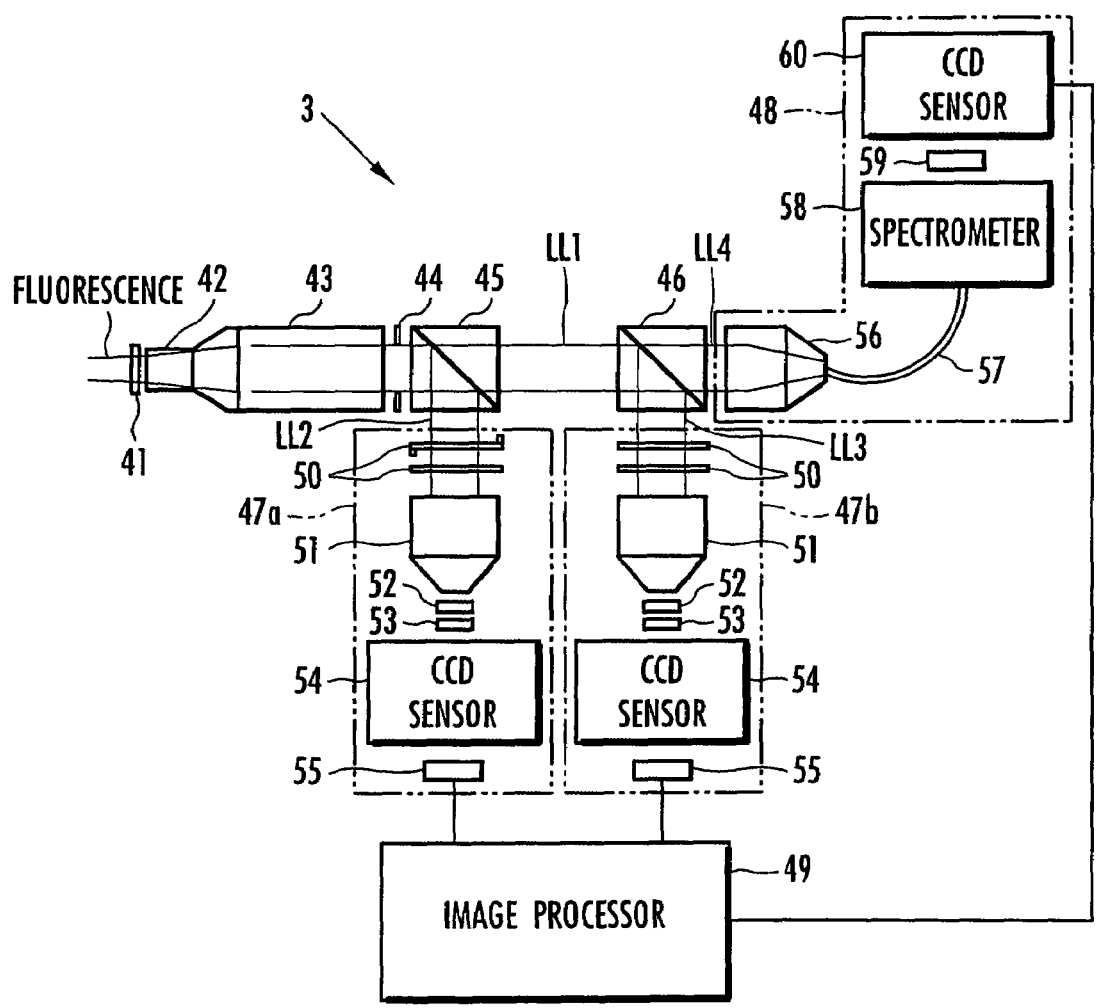
FIG. 3 is a block diagram showing the configuration of a fluorescence analytical processing unit included in the instrument shown in FIG. 2.

As shown in FIG. 3, the fluorescence analytical processing unit 3 has a filter 41, an objective lens group 42, a parallel ray generation lens group 43, and a flare/stray light cut plate 44 that sequentially allow passage of fluorescence produced by the gas in the condensed part Ex of the laser light L, on the side of its light receiving port.

The fluorescence produced in the condensed part Ex enters the filter 41, first. The filter 41 is for use in cutting off light having the wavelength (532 nm) of the laser light L, so that the filter 41 prevents scattered light from the laser light L from being taken into the fluorescence analytical processing unit 3. The fluorescence that has passed through the filter 41 enters the objective lens group 42, which magnifies a view of fluorescence produced in the condensed part Ex. Subsequently, the fluorescence enters the parallel ray generation lens group 43, which generates parallel rays from the fluorescence. In this instance, all lenses of the parallel ray generation lens group 43 are multi-coated for antireflection on the surface. In addition, the employed lenses have been corrected for spherical aberration, color, and other conditions. Light reflected on the lens surface or the like, however, still remains faintly in the fluorescence that has passed through the parallel ray generation lens group 43. Therefore, in this embodiment, the fluorescence that has passed through the parallel ray generation lens group 43 is guided to enter the flare/stray light cut plate 44 so that the flare/stray light cut plate 44 removes the reflected light remaining in the fluorescence.

The fluorescence analytical processing unit 3 further includes a 30% visible region beam splitter 45 and a 50% visible region beam splitter 46. The fluorescence that has passed through the flare/stray light cut plate 44 enters the 30% visible region beam splitter 45 and is divided into two components of fluorescence LL1 and L12 by the splitter 45. One of the components of fluorescence LL1 and LL2, namely the fluorescence LL1 further enters the 50% visible region beam splitter 46 and is divided into two components of fluorescence LL3 and LL4 by the splitter 46. Consequently, the fluorescence that enters the fluorescence analytical processing unit 3 is divided into three components of fluorescence LL2, L13, and LL4 in this embodiment.

The fluorescence analytical processing unit 3 includes imaging devices 47a and 47b for obtaining a view of fluorescence having a predetermined specific wavelength in a traveling path of the fluorescence LL2 and in a traveling path of the fluorescence LL3 of the fluorescence divided as described above, and includes an analyzer 48 for obtaining wavelength distribution data that indicates a wavelength distribution (spectrum distribution) of the fluorescence LL4 in a traveling path of the fluorescence LL4. Furthermore, the fluorescence analytical processing unit 3 includes an image processor 49 for generating image data or the like based on the view data (image data) obtained by the imaging devices 47a and 47b and the wavelength distribution data obtained by the analyzer 48.

The imaging devices 47a and 47b have the same structure, each having a two-step interference filter 50, an imaging lens 51, an electronic shutter 52, an aperture 53, and a CCD camera 54. The following description mainly focuses on the imaging device 47a. The fluorescence LL2 obtained from the 30% visible region beam splitter 45 enters the two-step interference filter 50. The two-step interference filter 50 is for use in extracting and passing only fluorescence having a wavelength within one angstrom ($10^{-10}$ m) around a predetermined specific wavelength out of the entering fluorescence LL2. In this instance, the two-step interference filter 50 allows the angle between the filter and a light beam entering it to be fine-tuned, which optimizes the transmittance of the fluorescence having the specific wavelength. The fluorescence having the specific wavelength extracted by the two-step interference filter 50 passes through the imaging lens 51, the electronic shutter 52, and the aperture 53 sequentially and thereafter an image is formed on the CCD camera 54. The imaging lens 51 has a zoom function so as to enlarge or reduce the fluorescence view in size. The electronic shutter 52 is open/close controlled in synchronization with the oscillation of the pulse laser 13, by which only the view of the fluorescence that occurs at the moment when the target inspection region E is irradiated with the laser light L or of the fluorescence that occurs after an elapse of several nanoseconds thereafter is formed on the CCD camera 54. View data of the fluorescence having the specific wavelength is then output from the CCD camera 54 to the image processor 49 via a Peltier cooling element 55. The Peltier cooling element 55 cools a CCD sensor (not shown) of the CCD camera 54 down to −30° C. or lower to reduce thermal noise that adversely affects the CCD sensor. Cooling the CCD sensor in this manner increases the sensitivity of the CCD sensor to approx. 1000 times higher than that of the CCD sensor at room temperature, and therefore the CCD sensor can detect weak fluorescence with high sensitivity.

The same applies to the imaging device 47b as the imaging device 47a described above. In this instance, the specific wavelength of the fluorescence imaged by the imaging devices 47a and 47b corresponds to a specific type of gas required to be observed. In this embodiment, the specific wavelength of the fluorescence imaged by the imaging device 47a is the wavelength (for example, 588 nm) of the fluorescence produced when helium is excited or ionized by the laser light L, and the specific wavelength of the fluorescence imaged by the imaging device 47b is the wavelength (for example, 656 nm) of the fluorescence produced when hydrogen is excited or ionized by the laser light L. The wavelengths of the fluorescence differ from the wavelength of the laser light L (532 nm) and they are within the visible light region.

If only a single type of gas is required to be observed as the specific type of gas, only one of the imaging devices 47a and 47b can be provided. For example, in this embodiment, one of the hydrogen and helium is supplied to the fuel cell stack FC in the gas leak inspection for the fuel cell stack FC. Therefore, only one of the imaging devices 47a and 47b is used to image the fluorescence having the specific wavelength corresponding to the hydrogen or helium.

The analyzer 48 includes a condenser lens 56, an optical fiber 57, a spectrometer 58, an electronic shutter 59, and a CCD sensor 60. The fluorescence LL4 entering the analyzer 48 from the 50% visible region beam splitter 46 is condensed by the condenser lens 56, first, and then transferred from the condenser lens 56 to the spectrometer 58 via the optical fiber 57. The condenser lens 56 is adjusted so as to have an N.A. value of 0.2 or so. The spectrometer 58 divides the input fluorescence LL4 according to wavelength and the CCD sensor 60 takes the views of linearly-arranged fluorescence divided according to wavelength. The view data is then output from the CCD sensor 60 to the image processor 49.

The following describes the operation of inspecting the fuel cell stack FC for a gas leak by using the instrument 1 according to this embodiment.

The pipe 5 is connected to the inspection object, namely the fuel cell stack FC placed on the base 4, and thereafter the fuel cell stack FC is supplied with gas for the gas leak inspection (hydrogen or helium) through the pipe 5. The laser light generating/transfer unit 2 is operated in this condition, by which the laser light generating means 10 generates pulsing laser light having the given wavelength (532 nm) as described above. Furthermore, the laser light transfer means 11 transfers the laser light L to irradiate the target inspection region E therewith so that the laser light L is condensed in the condensed part Ex within the target inspection region E. In the above, the pulse laser 13 of the laser light generating means 10 oscillates at 100 cycles per second, for example. Furthermore, the operation of the XY table 29 moves the condensed part Ex of the laser light L, which is applied to the target inspection region E, at a given speed (for example, 10 cm/sec) within the target inspection region E to scan the target inspection region E.

Every time the target inspection region E is irradiated with the pulsing laser light L, fluorescence occurs in the condensed part Ex of the laser light L along with the electrolytic dissociation (ionization), recombination, or deexcitation (namely, multiple photon ionization phenomenon) or along with excitation or deexcitation (namely, multiple photon excitation phenomenon) of gas existing there. In this instance, if there is no gas leak in the portion corresponding to (adjacent to) the condensed part Ex of the laser light L of the fuel cell stack FC or in the vicinity of the portion, the gas producing the fluorescence in the condensed part Ex is air (more specifically, nitrogen, oxygen, water vapor, and the like in the air). If there is a gas leak in the portion corresponding to (adjacent to) the condensed part Ex of the fuel cell stack FC or in the vicinity of the portion, the gas producing the fluorescence in the condensed part Ex includes hydrogen or helium as gas for gas leak inspection in addition to the air. If the gas for gas leak inspection is hydrogen, some of the hydrogen molecules are excited or ionized by injection of 17 eV or higher energy in the condensed part Ex of the laser light L by multiple photons, and subsequent deexcitation produces fluorescence having a wavelength (656 nm) in the visible light region. If the gas for gas leak inspection is helium, some of the helium atoms are excited or ionized by injection of 23 eV or higher energy in the condensed part Ex of the laser light L by multiple photons, and subsequent deexcitation produces fluorescence having a wavelength (588 nm) in the visible light region.

Then, the fluorescence analytical processing unit 3 receives the fluorescence produced in the condensed part Ex of the laser light L as described above. In the fluorescence analytical processing unit 3, the imaging device 47a or 47b takes a view of the fluorescence having the specific wavelength (588 nm) corresponding to helium or the specific wavelength (656 nm) corresponding to hydrogen in the fluorescence produced in the condensed part Ex of the laser light L and then the view data is captured into the image processor 49. In this instance, if helium is used as gas for gas leak inspection, the view data obtained by the imaging device 47a is captured into the image processor 49, and if hydrogen is used, the view data obtained by the imaging device 47b is captured into the image processor 49.

The image processor 49 stores the view data of the fluorescence obtained by the imaging device 47a or 47b with the view data being associated with the position of the condensed part Ex of the laser light L every time the target inspection region E is irradiated with the pulsing laser light L. It then synthesizes the view data corresponding to each condensed part Ex with the view data being associated with each position of the target inspection region E to create an image representing the distribution of the gas (hydrogen or helium) for use in gas leak inspection in the target inspection region E (hereinafter, the image is referred to as gas leak spatial distribution image) and to display it on a display unit, which is not shown. In the gas leak spatial distribution image, an area and therearound where gas leak of the fuel cell stack FC occurs are dense with the views of the fluorescence of the gas for gas leak inspection and the brightness of the view of the fluorescence is relatively high in the area where the gas leak occurs and in the vicinity thereof. The view of the fluorescence of the gas for gas leak inspection can be colored or the color can vary with the intensity of the fluorescence. The gas leak spatial distribution image corresponds to the image data in the present invention.

In the fluorescence analytical processing unit 3, the analyzer 48 generates view data of fluorescence for each wavelength of the fluorescence that occurs in the condensed part Ex of the laser light L and it is captured into the image processor 49. The image processor 49 then stores the view data obtained from the analyzer 48 with the view data being associated with the position of the condensed part Ex (the position within the target inspection region E) of the laser light L every time the target inspection region E is irradiated with the pulsing laser light L. The image processor 49 generates an image (hereinafter, referred to as wavelength distribution image) representing the wavelength distribution (spectrum distribution) of the fluorescence in each position (the position in the condensed part Ex) within the target inspection region E on the basis of the view data and then displays it on a display unit, which is not shown, appropriately (by a given operation of the image processor 49).

As described above, it is possible to detect whether there is a gas leak in the fuel cell stack FC, to identify a gas leak portion, and to detect the concentration of gas for gas leak inspection in the gas leak portion by analyzing the image displayed on the display unit of the image processor 49. For example, it is possible to detect whether there is a gas leak in the fuel cell stack FC or to identify the gas leak portion on the basis of the gas leak spatial distribution image. Moreover, if there is a gas leak, the concentration of the gas for gas leak inspection can be detected based on the wavelength distribution image corresponding to the position of the gas leak portion. A specific example related to the detection of the concentration will be described later.

Subsequently, a second embodiment of the present invention will be described with reference to FIG. 4. An instrument of this embodiment differs from the instrument 1 of the first embodiment only in a part of the configuration. Therefore, the same reference numerals as in the first embodiment denote the same parts as those of the instrument 1 of the first embodiment, and detailed description thereof will be omitted here. Similarly to the first embodiment, this embodiment is an embodiment of a laser analytical instrument and also an embodiment of a gas leak inspection instrument.

Figure 4:
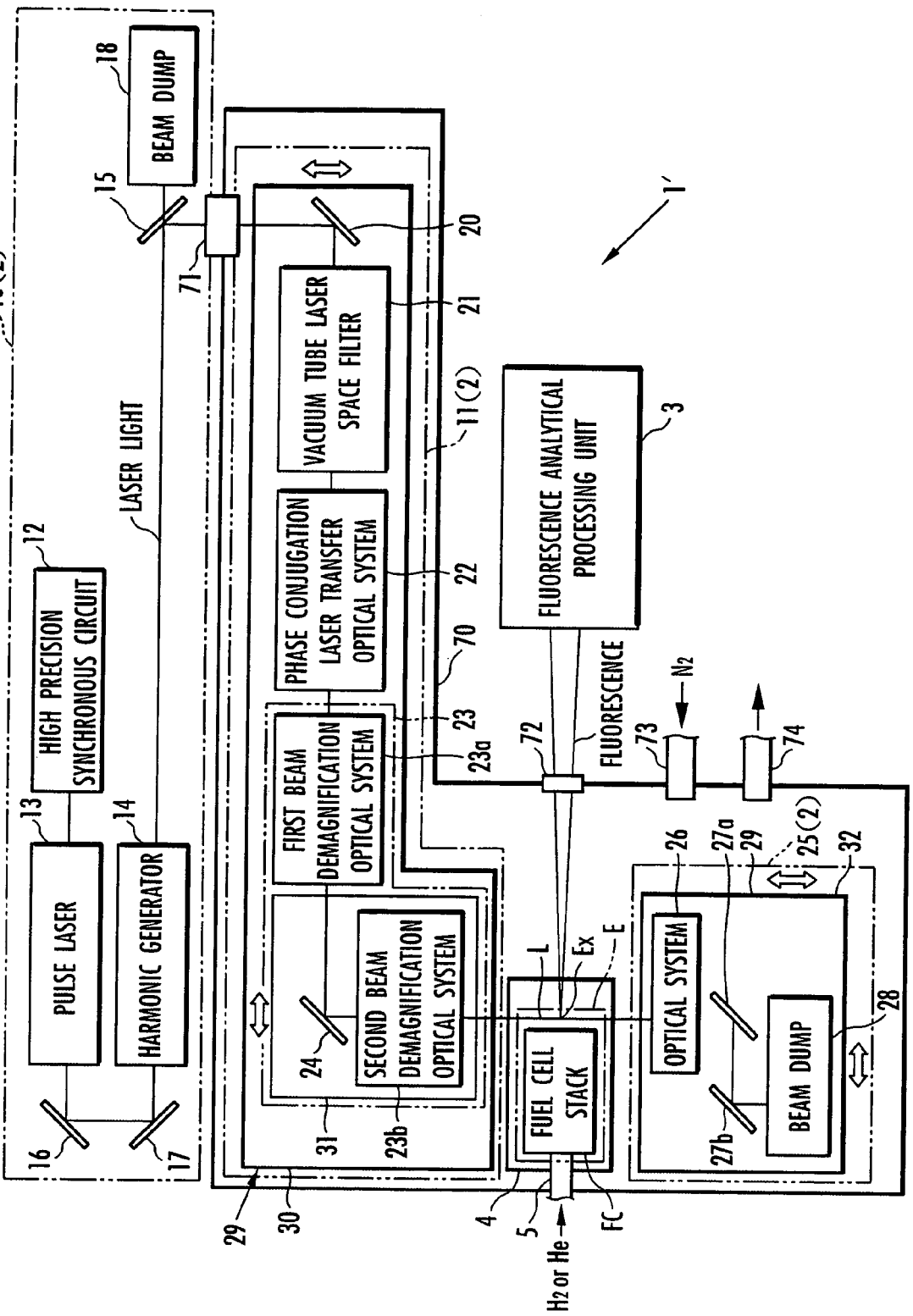
FIG. 4 is a block diagram showing the overall configuration of an instrument according to a second embodiment of a laser analytical instrument and a gas leak inspection instrument of the present invention.

Referring to FIG. 4, there is shown a block diagram of the overall configuration of the instrument of this embodiment. The instrument 1' is provided with a closed chamber 70. The closed chamber 70 houses laser light transfer means 11 of the laser light generating/transfer unit 2, the base 4 where the fuel cell stack FC is placed, and the laser light capturing means 25. A side wall of the closed chamber 70 is provided with a quartz window 71 (a transparent window made of quartz) on the optical axis of laser light (laser light reflected from the harmonic split mirror 15) output from the laser light generating means 10. Laser light output from the laser light generating means 10 is guided to the reflecting mirror 20 of the laser light transfer means 11 through the quartz window 71. Furthermore, a side wall of the closed chamber 70 is provided with a quartz window 72 facing a light receiving port of the fluorescence analytical processing unit 3, so that the fluorescence analytical processing unit 3 receives fluorescence produced in the condensed part Ex of the laser light L through the quartz window 72. Moreover, the closed chamber 70 is connected to a charge pipe 73 for supplying nitrogen to its internal space and to a discharge pipe 74 for discharging gas in the internal space.

The instrument 1' of this embodiment has the same configuration as the first embodiment except the above described components.

The following describes an operation of inspecting the fuel cell stack FC for a gas leak by using the instrument 1' of this embodiment.

In the instrument 1' of this embodiment, the gas leak inspection is conducted for the fuel cell stack FC as an inspection object on the base 4 with the air (atmospheric air) in the closed chamber 70 replaced with nitrogen. The operation differs from that of the instrument 1 of the first embodiment only in this point.

More specifically, the fuel cell stack FC as an inspection object is placed on the base 4 and is connected to the pipe 5 for supplying gas (hydrogen or helium) for gas leak inspection to the fuel cell stack FC. In this condition, nitrogen is supplied from a nitrogen feeder, which is not shown, to the closed chamber 70 through the charge pipe 73 and air in the closed chamber 70 is discharged from the closed chamber 70 through the discharge pipe 74. Thereby, the closed chamber 70 is filled with nitrogen.

Thereafter, the operation of the laser light generating/transfer unit 2 and that of the fluorescence analytical processing unit 3 are performed exactly alike in the first embodiment. In this instance, the fluorescence produced in the condensed part Ex of the laser light L is fluorescence corresponding to the nitrogen and/or fluorescence corresponding to the gas for gas leak inspection.

The instrument 1' of this embodiment is capable of increasing the resolution of concentration detection (a lower limit of detectable concentration) particularly when detecting the concentration of the gas for gas leak inspection on the basis of the view data of the wavelength distribution obtained from the analyzer 48 due to the less number of types of gas producing fluorescence. It is particularly effective when hydrogen is used as the gas for gas leak inspection, as explained in an example described later.

Although the gas leak inspection is conducted for the fuel cell stack FC in an open environment in the first embodiment, it can also be conducted in the closed chamber 70 as in the second embodiment.

Although the fuel cell stack FC as an inspection object is fixed on the base 4 and the condensed part Ex of the laser light L is moved in the first and second embodiments, it is also possible to move the fuel cell stack FC or the base 4 with the condensed part Ex of the laser light L fixed to be unmovable, as opposed to the above. To identify a gas leak portion of the fuel cell stack FC, however, the fuel cell stack FC is preferably fixed so as to be immovable as described in the first and second embodiments.

Furthermore, although the fuel cell stack FC is the object of the gas leak inspection in the first and second embodiments, the object of the gas leak inspection can be, for example, a hydrogen supply/discharge system (specifically, a hydrogen storage container, a hydrogen supply pump, a hydrogen supply/discharge pipe connected to the fuel cell stack FC, and so forth) for supplying hydrogen to the fuel cell stack FC or for discharging the supplied hydrogen from the fuel cell stack FC.

Figure 5:
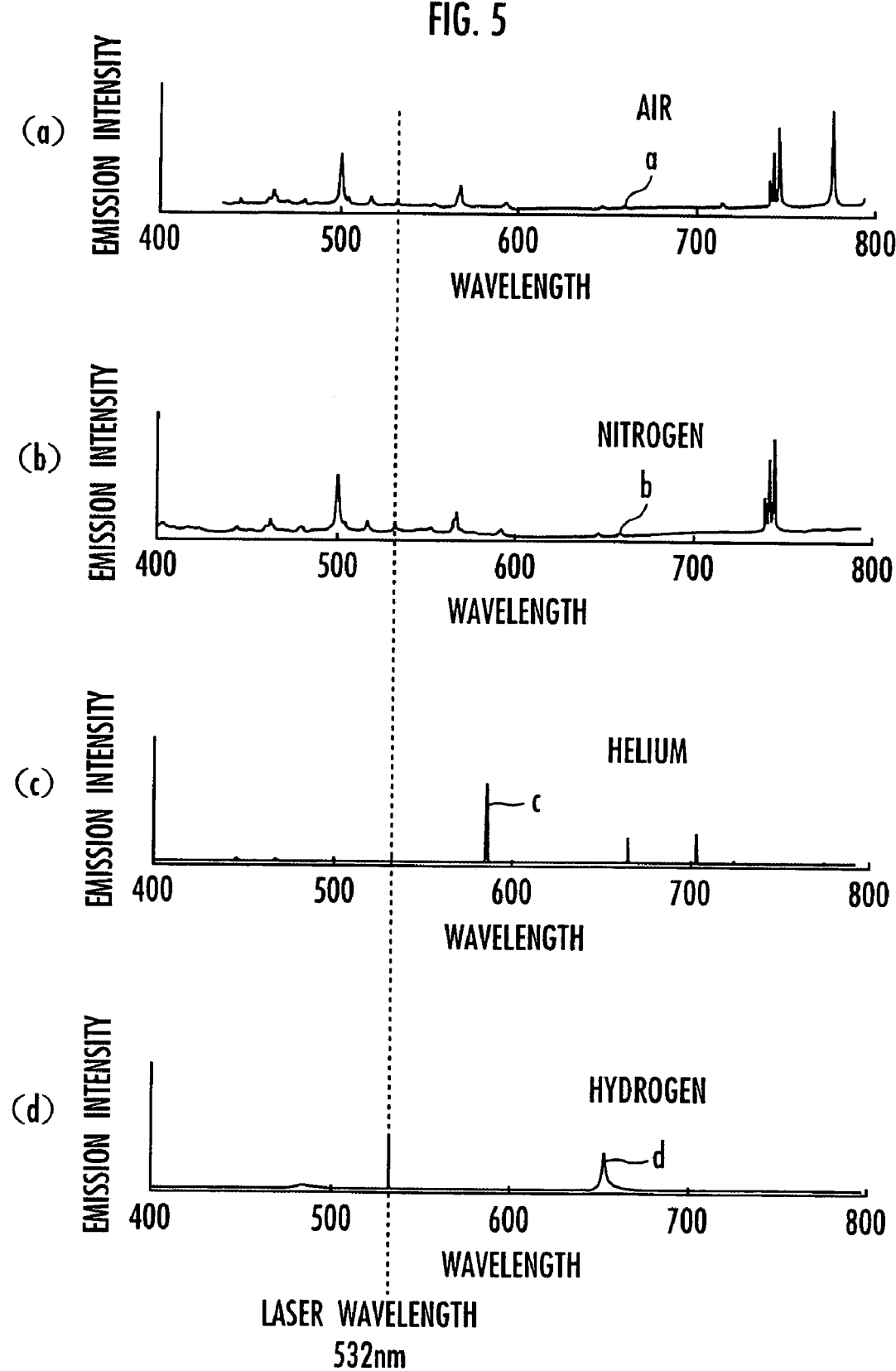
FIG. 5(a) to FIG. 5(d) are graphs showing measured data obtained by measuring the wavelength distributions of fluorescence from air, nitrogen, helium, and hydrogen, respectively.

Subsequently, examples of verification tests of the instrument 1 and instrument 1' of the first and second embodiments will be described with reference to FIG. 5 and FIG. 6. Incidentally, an environmental temperature is of the order of normal room temperature in both of Example 1 and Example 2 described hereinafter. In addition, the brightness around the instrument 1 or the instrument 1' including the condensed part Ex of the laser light is nearly equal to the normal room brightness.

EXAMPLE 1

A sealed glass tube containing a given type of gas was placed within the target inspection region E of the instrument 1 according to the first embodiment. In this condition, the laser light generating/transfer unit 2 was operated to irradiate the glass tube with the laser light L so that the condensed part Ex is located in the glass tube. During this time, the fluorescence analytical processing unit 3 received fluorescence produced in the glass tube and measured a wavelength distribution of the fluorescence on the basis of the view data obtained from the analyzer 48. The gas sealed in the glass tube includes four types: air, nitrogen, helium, and hydrogen.

The measurement result is shown in FIG. 5(a) to FIG. 5(d). FIG. 5(a) to FIG. 5(d) each show the wavelength distribution of the fluorescence when the gas sealed in the glass tube is air, nitrogen, helium, or hydrogen (more specifically, the intensity of the fluorescence for each wavelength within the range of 400 to 800 nm). In FIG. 5(a) to FIG. 5(d), an impulse part (hereinafter, referred to as emission line region in some cases) corresponds to a wavelength of the produced fluorescence.

As apparent from FIG. 5(a) and FIG. 5(b), the fluorescence from air or nitrogen is extremely low in the intensity of the wavelength component in the wavelength range of generally 580 to 740 nm. For example, the fluorescence from air or nitrogen has a 661 nm wavelength component (emission line region a, b) and its intensity is extremely low. On the other hand, as apparent from FIG. 5(c) and FIG. 5(d), the fluorescence from helium or hydrogen has a wavelength component whose intensity is relatively high in the wavelength range of 580 to 740 nm. More specifically, the fluorescence from helium is high in the intensity of, for example, a 588 nm wavelength component (emission line region c), and the fluorescence from hydrogen is high in the intensity of, for example, a 656 nm wavelength component (emission line region d). Although the wavelength 656 nm of the emission line region d of hydrogen is close to the wavelength 661 nm of the emission line regions a and b of air and nitrogen, the intensity of the emission line region d of hydrogen is sufficiently higher than the intensities of the emission line regions a and b of air and nitrogen.

Therefore, it is understood that, if helium is used as gas for gas leak inspection, it is possible to recognize the existence of helium in the condensed part Ex of the laser light L (the occurrence of a gas leak in the vicinity thereof in the fuel cell-stack FC) by observing the 588 nm wavelength component in the produced fluorescence in both of the first and second embodiments.

Similarly, it is understood that, if hydrogen is used as gas for gas leak inspection, it is possible to recognize the existence of hydrogen in the condensed part Ex of the laser light L (the occurrence of a gas leak in the vicinity thereof in the fuel cell stack FC) by observing the 656 nm wavelength component in the produced fluorescence in both of the first and second embodiments.

Incidentally, the emission line region of the helium is not broadened almost at all, while the emission line region of the hydrogen or nitrogen is slightly broadened. The reason is as follows. Since hydrogen or nitrogen gas is a diatomic molecule, it is excited or ionized by laser light and the molecule is dissociated into individual atoms: these atoms vibrate intensely in directions opposite to each other (the direction of getting closer or farther). Therefore, the Doppler shift occurs in the fluorescence produced during the deexcitation of the hydrogen or nitrogen atoms. As a result, it is considered that the emission line region of the fluorescence is broadened. On the other hand, the helium gas is a monoatomic molecule, so that, even if it is excited or ionized by laser light, no atomic vibration occurs unlike hydrogen or nitrogen. Therefore, the Doppler shift does not occur in the fluorescence produced during the deexcitation of the helium atoms. As a result, it is considered that the emission line region of the fluorescence is not broadened.

EXAMPLE 2

Preparing a sealed glass tube containing nitrogen gas that includes hydrogen (hereinafter, referred to as glass tube 1) and a sealed glass tube containing air gas that includes hydrogen (hereinafter, referred to as glass tube 2), the glass tubes 1 and 2 were placed within the target inspection region E of the instrument 1 according to the first embodiment. In this condition, the laser light generating/transfer unit 2 was operated to irradiate the glass tubes 1 and 2 with the laser light L with the condensed part Ex being located in the glass tubes 1 and 2. During this time, the fluorescence analytical processing unit 3 received fluorescence produced in the glass tubes 1 and 2 and measured a wavelength distribution of the fluorescence in the wavelength range of 653 nm to 663 nm on the basis of the view data obtained from the analyzer 48. In this instance, for the glass tube 1, the concentrations of the hydrogen were set to four types: 50 ppm, 100 ppm, 500 ppm, and 1000 ppm. For the glass tube 2, the concentrations of the hydrogen were set to five types: 100 ppm, 500 ppm, 1500 ppm, 4600 ppm, and 10000 ppm.

The measurement results are shown in FIG. 6(a) and FIG. 6(b). FIG. 6(a) and FIG. 6(b) show the wavelength distributions of the fluorescence of the glass tube 1 and the glass tube 2, respectively. In FIG. 6(a) and FIG. 6(b), the wavelength (approx. 656 nm) represented by the "hydrogen emission line" indicates the wavelength of the fluorescence from the hydrogen and the wavelength (approx. 661 nm) represented by the "nitrogen emission line" indicates the wavelength of the fluorescence from the nitrogen.

Referring to FIG. 6(a), regarding the detection of the hydrogen in the nitrogen gas, correlation between the hydrogen concentration and the signal strength of the fluorescence having a wavelength of approx. 656 nm (656.5 nm) was observed under the condition that the hydrogen concentration is chiefly 100 ppm or higher. When the hydrogen concentration was lower than 100 ppm, it was difficult to detect the hydrogen in distinction between hydrogen and nitrogen due to the effect of the fluorescence from the nitrogen having the peak intensity at approx. 661 nm (See the graph corresponding to the hydrogen concentration of 50 ppm in FIG. 6(a)).

From the above result, it is understood that, if hydrogen exists in the target inspection region E in the closed chamber 70 in an environment where the closed chamber 70 is filled with nitrogen as in the second embodiment, it is possible to detect the existence of the hydrogen and to detect the hydrogen concentration on the basis of the output data (view data) from the analyzer 48 and the output data (view data) from the imaging device 47 when the hydrogen concentration is equal to or higher than approx. 100 ppm.

Moreover, referring to FIG. 6(b), regarding the detection of the hydrogen in the air, correlation between the hydrogen concentration and the signal strength of the fluorescence having the wavelength of approx. 656 nm (656.5 nm) was observed under the condition that the hydrogen concentration is chiefly 500 ppm or higher. When the hydrogen concentration was lower than 500 ppm, it was difficult to detect the original hydrogen in distinction between the original hydrogen and hydrogen produced by the dissociation of water vapor due to an increase in the fluorescence of hydrogen produced by the dissociation of water vapor or moisture included in the air, which is caused by the laser light L, relative to the fluorescence of the original hydrogen added to the air. The intensity of the fluorescence having the wavelength corresponding to the "hydrogen emission line" in FIG. 6(b) includes that of the fluorescence of hydrogen produced by the dissociation of water vapor or moisture.

From the above result, it is understood that, if hydrogen exists in the target inspection region E in an atmospheric environment as in the first embodiment, it is possible to detect the existence of the hydrogen on the basis of the output data (view data) from the analyzer 48 and the output data (view data) from the imaging device 47 when the hydrogen concentration is equal to or higher than approx. 500 ppm. According to an experiment conducted by the present inventor, the hydrogen concentration can also be detected in the range of approx. 500 ppm to 30000 ppm in atmospheric environment.

Although it is possible to detect the existence of hydrogen up to the hydrogen concentration of 100 ppm or 500 ppm in the above Example 2, the detectable concentration depends upon the brightness around the instrument of the embodiment, a performance of the fluorescence analytical processing unit 3, power of the laser light, and the like. The detectable limit of the hydrogen concentration can be higher than 100 ppm or 500 ppm or can be lower than those, if necessary.

INDUSTRIAL APPLICABILITY

As described hereinabove, the present invention is useful as a technique for detecting the existence of various types of gas or the concentration thereof or detecting a gas leak in various types of inspection objects such as a fuel cell stack. Particularly, it is useful as a technique for detecting hydrogen or helium, which has been difficult to be achieved by a conventional laser device.

The invention claimed is:

1. A laser analytical instrument for producing fluorescence having a wavelength corresponding to the type of object gas of analysis by exciting the object gas of analysis by laser light and then analyzing the state of the object gas of analysis on the basis of the state of the fluorescence, the laser analytical instrument comprising:
    laser light generating means for generating a single laser light having a given wavelength and top-hat type power density distribution;
    a demagnification optical system for emitting the laser light generated by the laser light generating means toward an area where the object gas of analysis exists so as to be condensed into a point in the area where the object gas of analysis exists;
    a phase conjugation laser transfer optical system provided in an optical path of the laser light from the laser light generating means to the demagnification optical system; and
    fluorescence analysis means for analyzing the state of the received fluorescence, the received fluorescence being produced from the object gas of analysis in the condensed part of the laser light,
    wherein, when the object gas of analysis comprises hydrogen, the laser light is imparted with energy that injects 17 electron-volts or higher energy into each of one or more hydrogen molecules of the object gas to cause a multiple photon ionization phenomenon or a multiple photon excitation phenomenon of the one or more hydrogen molecules to produce fluorescence in a visible light region from the one or more hydrogen molecules.

2. The laser analytical instrument according to claim 1, wherein a peak intensity in the condensed part of the laser light is $10^{14}$ W/cm$^2$ or higher.

3. A gas leak inspection instrument for inspecting an inspection object having a gas passage inside for a gas leak by using the laser analytical instrument according to claim 1, the gas leak inspection instrument comprising means for supplying hydrogen to the inside of the inspection object, wherein the laser light is emitted from the demagnification optical system in such a way that the condensed part of the laser light exists in the vicinity of the inspection object in the supply state of the hydrogen, and detects whether there is a leak of hydrogen from inside of the inspection object to outside of the inspection object.

4. The gas leak inspection instrument according to claim 3, wherein the inspection object is a fuel cell stack, a hydrogen supply system for supplying hydrogen to the fuel cell stack, or a hydrogen discharge system for discharging the hydrogen from the fuel cell stack.

5. The gas leak inspection instrument according to claim 3, wherein when hydrogen is supplied to the inspection object, the laser light is emitted toward the vicinity of the inspection object at least in the state where the inspection object is housed in a closed chamber filled with nitrogen.

6. The gas leak inspection instrument according to claim 3, further comprising moving means for relatively moving the condensed part of the laser light with respect to the inspection object.

7. The gas leak inspection instrument according to claim 6, wherein the fluorescence analysis means includes means for generating image data indicating a relation between a relative position of the condensed part of the laser light with respect to the inspection object and the intensity of fluorescence having a wavelength corresponding to hydrogen in the fluorescence produced in the condensed part.

8. A laser analytical method for producing fluorescence having a wavelength corresponding to the type of object gas of analysis by exciting the object gas of analysis by single laser light, and then analyzing the state of the object gas of analysis on the basis of the state of the fluorescence, the laser analytical method comprising the steps of:
providing a phase conjugation laser transfer optical system in an optical path of the laser light from laser light generating means to demagnification optical system;
emitting the single laser light having a given wavelength and top-hat type power density distribution toward an area where the object gas of analysis exists so as to condense the laser light into a point in the area where the object gas of analysis exists;
when the object gas of analysis comprises hydrogen, causing a multiple photon ionization phenomenon or a multiple photon excitation phenomenon of one or more hydrogen molecules of the object gas using the single laser light imparted with energy that injects 17 electron-volts or higher energy into each of the one or more hydrogen molecules to cause a multiple photon ionization phenomenon or a multiple photon excitation phenomenon of the one or more hydrogen molecules to produce fluorescence in a visible light region from the one or more hydrogen molecules; and
receiving the produced fluorescence and analyzing the state of the fluorescence.

9. The laser analytical method according to claim 8, wherein a peak intensity in the condensed part of the laser light is $10^{14}$ W/cm$^2$ or higher.

10. A gas leak inspection instrument for inspecting an inspection object for a gas leak, the inspection object being a fuel cell stack, a hydrogen supply system for supplying hydrogen to the fuel cell stack, or a hydrogen discharge system for discharging the hydrogen from the fuel cell stack, the gas leak inspection instrument comprising:
laser light irradiation means for emitting at least one beam of laser light toward the vicinity of the inspection object;
means for supplying hydrogen to the inside of the inspection object; and
analysis means for analyzing the state of a received light and detecting whether there is a leak of hydrogen from inside of the inspection object to outside of the inspection object, the received light being generated in the vicinity of the inspection object in the state where hydrogen is supplied to the inspection object, wherein the laser light is imparted with energy that injects 17 electron-volts or higher energy into each of the one or more hydrogen molecules to cause a multiple photon ionization phenomenon or a multiple photon excitation phenomenon of the one or more hydrogen molecules to produce fluorescence in a visible light region from the one or more hydrogen molecules.

11. The gas leak inspection instrument according to claim 10, further comprising moving means for relatively moving the irradiated position of the laser light with respect to the inspection object.

12. The gas leak inspection instrument according to claim 11, wherein the fluorescence analysis means includes means for generating image data indicating a relation between a relative position of the laser light irradiated position with respect to the inspection object and the intensity of light having a wavelength corresponding to hydrogen in the light produced in the condensed part.

13. A laser analytical instrument for producing fluorescence having a wavelength corresponding to the type of object gas of analysis by exciting the object gas of analysis by laser light and then analyzing the state of the object gas of analysis on the basis of the state of the fluorescence, the laser analytical instrument comprising:
laser light generating means for generating a single laser light having a given wavelength and top-hat type power density distribution;
a demagnification optical system for emitting the laser light generated by the laser light generating means toward an area where the object gas of analysis exists so as to be condensed into a point in the area where the object gas of analysis exists;
a phase conjugation laser transfer optical system provided in an optical path of the laser light from the laser light generating means to the demagnification optical system; and
fluorescence analysis means for analyzing the state of the received fluorescence, the received fluorescence being produced from the object gas of analysis in the condensed part of the laser light,
wherein, when the object gas of analysis comprises helium, the laser light is imparted with energy that injects 23 electron-volts or higher energy into each of one or more helium molecules of the object gas to cause a multiple photon ionization phenomenon or a multiple photon excitation phenomenon of the one or more helium molecules to produce fluorescence in a visible light region from the one or more helium molecules.

14. A laser analytical method for producing fluorescence having a wavelength corresponding to the type of object gas of analysis by exciting the object gas of analysis by single laser light, and then analyzing the state of the object gas of analysis on the basis of the state of the fluorescence, the laser analytical method comprising the steps of:
providing a phase conjugation laser transfer optical system in an optical path of the laser light from laser light generating means to demagnification optical system;
emitting the single laser light having a given wavelength and top-hat type power density distribution toward an area where the object gas of analysis exists so as to condense the laser light into a point in the area where the object gas of analysis exists;
when the object gas of analysis comprises helium, causing a multiple photon ionization phenomenon or a multiple photon excitation phenomenon of one or more helium molecules of the object gas using the single laser light imparted with energy that injects 23 electron-volts or higher energy into each of the one or more helium molecules to cause a multiple photon ionization phenomenon or a multiple photon excitation phenomenon of the one or more helium molecules to produce fluorescence in a visible light region from the one or more helium molecules; and receiving the produced fluorescence and analyzing the state of the fluorescence.

15. A gas leak inspection instrument for inspecting an inspection object for a gas leak, the inspection object being a fuel cell stack, a hydrogen supply system for supplying hydrogen to the fuel cell stack, or a hydrogen discharge system for discharging the hydrogen from the fuel cell stack, the gas leak inspection instrument comprising:

laser light irradiation means for emitting at least one beam of laser light toward the vicinity of the inspection object;

means for supplying helium to the inside of the inspection object; and analysis means for analyzing the state of a received light and detecting whether there is a leak of helium from inside of the inspection object to outside of the inspection object, the received light being generated in the vicinity of the inspection object in the state where helium is supplied to the inspection object, wherein the laser light is imparted with energy that injects 23 electron-volts or higher energy into each of the one or more helium molecules to cause a multiple photon ionization phenomenon or a multiple photon excitation phenomenon of the one or more helium molecules to produce fluorescence in a visible light region from the one or more helium molecules.

* * * * *